(12) United States Patent
Sadowski et al.

(10) Patent No.: US 10,495,571 B2
(45) Date of Patent: Dec. 3, 2019

(54) METHOD AND APPARATUS FOR MONITORING SURFACE PHENOMENA

(71) Applicant: BioNavis Oy, Ylöjärvi (FI)

(72) Inventors: Janusz Sadowski, Tampere (FI); Niko Granqvist, Ylöjärvi (FI); Jussi Tuppurainen, Julkujärvi (FI); Annika Jokinen, Helsinki (FI)

(73) Assignee: BioNavis Oy, Ylojarvi (FI)

( * ) Notice: Subject to any disclaimer, the term of this patent is extended or adjusted under 35 U.S.C. 154(b) by 289 days.

(21) Appl. No.: 15/123,258

(22) PCT Filed: Feb. 18, 2015

(86) PCT No.: PCT/FI2015/050095
§ 371 (c)(1),
(2) Date: Sep. 2, 2016

(87) PCT Pub. No.: WO2015/132456
PCT Pub. Date: Sep. 11, 2015

(65) Prior Publication Data
US 2017/0067826 A1  Mar. 9, 2017

(30) Foreign Application Priority Data
Mar. 5, 2014  (FI) ...................... 20145207

(51) Int. Cl.
*G01N 21/552* (2014.01)
*G01N 21/77* (2006.01)
*G01N 33/543* (2006.01)

(52) U.S. Cl.
CPC ........... *G01N 21/553* (2013.01); *G01N 21/77* (2013.01); *G01N 33/54373* (2013.01); *G01N 2021/7773* (2013.01); *G01N 2201/126* (2013.01)

(58) Field of Classification Search
CPC . G01N 21/553; G01N 21/77; G01N 33/54373
See application file for complete search history.

(56) References Cited

U.S. PATENT DOCUMENTS

| 2007/0046943 A1 | 3/2007 | VanWiggeren et al. |
| 2010/0128273 A1 | 5/2010 | Lee et al. |
| 2013/0189797 A1 | 7/2013 | Quinn |

FOREIGN PATENT DOCUMENTS

KR  20100035275 A  4/2010

OTHER PUBLICATIONS

Bionavis, How Does Surface Plasmon Resonance Work?, Feb. 20, 2013, Retrieved from http://faculty.missouri.edu/~glaserr/3700s13/SP13A04_SPR.pdf, 6 pages.

(Continued)

*Primary Examiner* — Melanie Brown
(74) *Attorney, Agent, or Firm* — Ziegler IP Law Group, LLC

(57) ABSTRACT

A method for monitoring surface phenomena includes
measuring a first surface plasmon resonance angle value ($\phi_{SPR,REF}$) of a sample region (REG1),
measuring a first critical angle value ($\phi_{TIR,REF}$) of the sample region (REG1), causing a change of surface concentration ($c_{M1,SRF}$) of an analyte (M1) at the sample region (REG1),
changing the bulk composition at the sample region (REG1),
measuring a second surface plasmon resonance angle value ($\phi_{SPR}(t)$) of the sample region (REG1),
measuring a second critical angle value ($\phi_{TIR}(t)$) of the sample region (REG1), and
determining an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and wherein the magnitude ($\phi_{COMP}$) of said effect is determined by using the second critical angle value ($\phi_{TIR}(t)$).

6 Claims, 13 Drawing Sheets

(56) References Cited

OTHER PUBLICATIONS

Liang et al., "Surface plasmon resonance instrument as a refractometer for liquids and ultrathin films", Sensors and Actuators B: Chemical Available Online Jun. 16, 2010, journal hopepage: www.elsevier.com/locate/snb, 10 pages.

Nizamov et al., "Self-refrencing SPR-biosensors based on penetration difference of evanescent waves", Biosensors and Bioelectronics, Available online Jul. 23, 2011, journal homepage: www.elsevier.com/locate/bios, 8 pages.

Narayan et al., "Determining selectivity of psosphoinositide-binding domais", Science Direct, Methods 39 (2006) 122-133, May 1, 2006, www.elsevier.com/locate/ymeth, doi: 10.1016/j.ymeth.2006.05.006, 13 pages.

'Surface plasmon resonance', Wikipedia, Retrieved at https://web.archive.org/web/20120830105229, http://en.wikipedia.org/wiki/Surface_Plasmon_Resonance, Aug. 30, 2012, 8 pages.

International Search Report, Application No. PCT/FI2015/050095, dated May 19, 2015, 4 pages.

Jung et al: "Quantitative Interpretation of the Response of Surface Plasmon Resonance Sensors to Adsorbed Films", Langmuir, vol. 14, No. 19 (1997), 13 pages.

Liang et al.: "Surface plasmon resonance instrument as a refractometer for liquids and ultrathin films", Sensors and actuators B: Chemical: International journal devoted to research and development of physical and chemical transducers, Elsevier BV, NL, vol. 149, No. 1, (2010), 9 pages.

Jääskeläinen et al.: "On Reflectometric Measurement of a Refractive Index of Milk", Journal of dairy science, American dairy science association, US, vol. 84, No. 1 (2001); 6 pages.

Chinowsky: "Optical multisensors based on surface plasmon resonance", Dissertation, 2000; 191 pages.

Sulyma et al.: "Surface plasmon resonance as a probe of interactions between a thin-film gold electrode and an aqueous supporting electrolyte containing 1-ethyl-3-methylimidazolium ethyl sulfate ionic liquid : SPR as a probe of ionic liquid interactions with a gold film electrode", Surface and\ interface analysis, vol. 44, No. 7 (2011); 1'0 pages.

Search Report, European Patent Office; dated Oct. 2, 2017 for the parallel European patent application No. 15758503.5., 10 pages.

METHOD AND APPARATUS FOR MONITORING SURFACE PHENOMENA

FIELD

Some embodiments of the invention relate to monitoring surface phenomena by using surface plasmon resonance.

BACKGROUND

Binding of molecules to a functional layer may be studied e.g. by attaching fluorescent or other (e.g. radioactive) labels to molecules. The labeled molecules may occupy active sites of the functional layer, and the amount of labeled molecules attached to the functional layer may be monitored based on intensity of fluorescence excited in the labeled molecules. However, it may be difficult or impossible to attach labels to certain types of molecules. The labels may also have an effect on the chemical and physical properties of the labeled molecules.

SUMMARY

Some embodiments relate to a method for monitoring surface phenomena. Some embodiments relate to an apparatus for monitoring surface phenomena. Some embodiments relate to a computer program for monitoring surface phenomena. Some embodiments relate to a computer program product, which comprises computer program code for monitoring surface phenomena.

According to an aspect, there is provided a method comprising:

measuring a first surface plasmon resonance angle value ($\phi_{SPR,REF}$) of a sample region (REG1), measuring a first critical angle value ($\phi_{TIR,REF}$) of the sample region (REG1), causing a change of surface concentration ($c_{M1,SRF}$) of an analyte (M1) at the sample region (REG1), changing the bulk composition at the sample region (REG1), measuring a second surface plasmon resonance angle value ($\phi_{SPR}(t)$) of the sample region (REG1), measuring a second critical angle value ($\phi_{TIR}(t)$) of the sample region (REG1), and determining an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and wherein the magnitude ($\phi_{COMP}$) of said effect is determined by using the second critical angle value ($\phi_{TIR}(t)$).

According to an aspect, there is provided an apparatus (500) comprising at least one processor (CNT1), a memory (MEM3) including computer program code (PROG1), the memory (MEM3) and the computer program code (PROG1) being configured to, with the at least one processor (CNT1), cause the apparatus (500) to perform at least the following:

measure a first surface plasmon resonance angle value ($\phi_{SPR,REF}$) of a sample region (REG1) when the sample region (REG1) has a first surface concentration ($c_{M1,SRF}(t_{1A})$) of an analyte (M1) and first bulk composition ($c_{M3}(t_{1A})$), measure a first critical angle value ($\phi_{TIR,REF}$) of the sample region (REG1), measure a second surface plasmon resonance angle value ($\phi_{SPR}(t)$) of the sample region (REG1) when the sample region (REG1) has a second surface concentration ($c_{M1,SRF}$) of an analyte (M1) and second bulk composition ($c_{M3}(t_{1B})$), measure a second critical angle value ($\phi_{TIR}(t)$) of the sample region (REG1), and determine an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and wherein the magnitude ($\phi_{COMP}$) of said effect is determined by using the second critical angle value ($\phi_{TIR}(t)$).

According to an aspect, there is provided a computer readable medium (MEM3) comprising computer program (PROG1) configured to, when executed by at least one processor (CNT1), cause an apparatus (500) to perform at least the following:

measure a first surface plasmon resonance angle value ($\phi_{SPR,REF}$) of a sample region (REG1) when the sample region (REG1) has a first surface concentration ($c_{M1,SRF}(t_{1A})$) of an analyte (M1) and first bulk composition ($c_{M3}(t_{1A})$), measure a first critical angle value ($\phi_{TIR,REF}$) of the sample region (REG1), measure a second surface plasmon resonance angle value ($\phi_{SPR}(t)$) of the sample region (REG1) when the sample region (REG1) has a second surface concentration ($c_{M1,SRF}(t_{1B})$) of an analyte (M1) and second bulk composition ($c_{M3}(t_{1B})$), measure a second critical angle value ($\phi_{TIR}(t)$) of the sample region (REG1), and determine an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and wherein the magnitude ($\phi_{COMP}$) of said effect is determined by using the second critical angle value ($\phi_{TIR}(t)$).

The method may be implemented by using a sample region, which comprises a substantially transparent substrate, a thin layer of electrically conductive material, and a dielectric sample. The electrically conductive material may be a metal. For example, the sample region may comprise a thin layer of gold deposited on a glass substrate, and the dielectric sample may comprise an aqueous solution. The sample region may be illuminated with a substantially monochromatic input light beam, and the reflectance of the sample region may be measured as a function of the reflection angle $\phi$ of the output beam. The measured reflectance curve may be used for determining a surface plasmon resonance angle and a critical angle of total internal reflection. The sample region may have a sample volume. The sample volume may comprise a resonance volume, wherein the thickness of the resonance volume may be substantially smaller than the thickness of the sample volume. The surface plasmon resonance angle may provide information about the material layers and bulk material located within the resonance volume, wherein the critical angle may provide information about the material layers and bulk material located within the thicker sample volume. The contribution of the bulk material may be determined from the critical angle, and the contribution of the bulk material may be taken into account when determining information about the material layers located within the sample region. In particular, the contribution of the bulk material may be subtracted from a surface plasmon resonance angle value in order to provide an indicator value, which is indicative of the surface concentration of an analyte in the sample volume.

In an embodiment, the method may be used for monitoring surface concentration of an analyte without using fluorescent, or any other labels. The method may be used for monitoring surface concentration of analyte molecules in a situation where the analyte molecules are non-labelled.

BRIEF DESCRIPTION OF THE DRAWINGS

In the following examples, several variations will be described in more detail with reference to the appended drawings, in which.

DETAILED DESCRIPTION

Figure 1A:
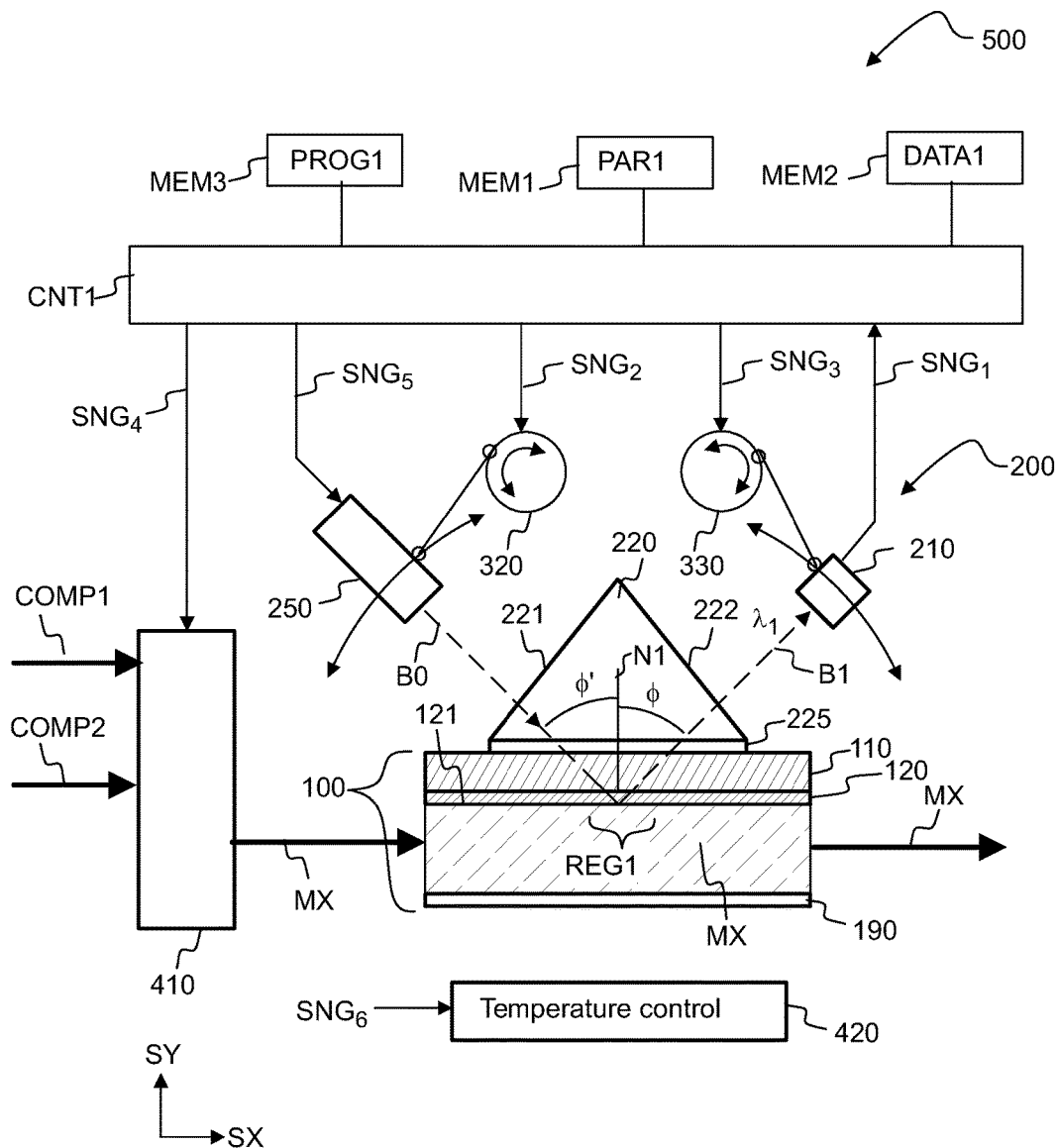
FIG. 1a shows, by way of example, in a cross sectional view, a measuring apparatus, which comprises a surface plasmon resonance sensor.

Referring to FIG. 1a, a measuring apparatus 500 may comprise a surface plasmon resonance sensor 200 (i.e. an SPR sensor 200). The SPR sensor 200 may comprise a substrate 110, a conductive layer 120, a coupling element 220, a light source 250, and an optical detector 210.

The light source 250 may be arranged to provide an input beam B0. The input beam B0 may be a collimated beam or a converging (focused) beam. The input beam B0 may be arranged to impinge on a sample region REG1 of the conductive layer 120. The sample region REG1 may be arranged to provide a reflected beam B1 by reflecting light of the input beam B0. The sample region REG1 may also be called e.g. as a sensor region REG1.

The sample region REG1 may have a surface normal N1. The surface normal N1 is perpendicular to the plane of the conductive layer 120. The input angle (V may denote the angle between the normal N1 and the direction of propagation of the input beam B0. The reflection angle φ may denote the angle between the normal N1 and the direction of propagation of the output beam B1. The reflection angle φ may be equal to the input angle φ'.

The apparatus 500 may comprise an actuator 320 for changing the direction of the centerline of the input beam B0. In particular, the actuator 320 may be arranged to change the input angle φ'. The detector 210 may be arranged to monitor the intensity of a reflected beam B1. The apparatus 500 may comprise an actuator 330 for changing the position of the detector 210. The reflection angle φ may be scanned by changing the position of the detector 210. The position of the detector 210 may be changed in order to change the reflection angle φ of the reflected beam B1, whose intensity is monitored by using the detector 210.

In an embodiment, the direction of the input beam B0 and the position of the detector 210 may be changed by using the same actuator 320. The actuator 320 may comprise e.g. a stepper motor or an electromagnet, which may be arranged to mechanically move at least one optical component of the light source 250.

The light source 250 may comprise e.g. a laser, a light emitting diode (LED), a discharge lamp, or an incandescent lamp. The detector 210 may be arranged to monitor the intensity $I_1$ of the reflected beam B1. The detector 210 may be arranged to provide a detector signal $SNG_1$ indicative of the spectral intensity of the reflected beam B1 at the wavelength $\lambda_1$. The detector 210 may be arranged to provide a detector signal $SNG_1$, which is indicative of the intensity of reflected light B1, which has the wavelength $\lambda_1$ and the reflection angle φ.

The light of the input beam B0 may be substantially monochromatic and/or the reflected light B1 may be detected by using spectrally selective detection. The detector 210 and/or the light source 250 may comprise one or more optical filters in order to provide spectral selectivity. The spectral width of the input beam B0 may be e.g. smaller than or equal to 20 nm, smaller than or equal to 10 nm, smaller than or equal to 5 nm, or even smaller than or equal to 1 nm. The spectral width of a passband of an optical filter may be e.g. smaller than or equal to 20 nm, smaller than or equal to 10 nm, smaller than or equal to 5 nm, or even smaller than or equal to 1 nm. The detector 210 may be arranged to measure the intensity of p-polarized light reflected from the sample region REG1. The light of the input beam B0 may be p-polarized.

The coupling element 220 may be e.g. a prism, which has an input facet 221 and an output facet 222. The input facet 221 may be inclined so as to allow total internal reflection at the sample region REG1, and the output facet 222 may be inclined so as to allow coupling of the reflected beam B0 out of the element 220.

In an embodiment, the coupling element 220 may also be a transparent plate, which has an input grating 221 and/or an output grating 222. The material of the coupling element 220 may be transparent at the wavelength $\lambda_1$.

The substrate 110 may be a substantially planar plate. The substrate 110 may comprise e.g. glass, quartz ($SiO_2$), plastic or aluminum oxide ($Al_2O_3$). The conductive layer 120 may be e.g. a metal layer. The conductive layer 120 may comprise e.g. gold, platinum, silver, copper, aluminum, titanium and/or chromium. The thickness of the conductive layer may be e.g. smaller than or equal to 100 nm. The conductive layer 120 may be e.g. a metal film, which has been deposited on the substrate 110. The conductive layer 120 may be in contact with a sample MX. The conductive layer 120 may have a surface 121, which is in contact with a sample MX.

The sensor 200 may optionally comprise coupling material 225. The coupling material 225 may comprise e.g. transparent elastomer (e.g. silicone rubber) or index matching oil. The coupling material 225 may be arranged to couple the input beam B0 from the coupling element 220 into the substrate 110, and to couple the reflected beam B1 from the substrate 110 into the element 220.

The apparatus 500 may comprise a control unit CNT1, which may be arranged to control operation of the sensor 200. The control unit CNT1 may receive the detector signal $SNG_1$ from the detector 210.

The control unit CNT1 may be arranged to vary the reflection angle $\phi$ and to record the intensity of the reflected light B1 as a function of the reflection angle $\phi$. In an embodiment, the composition of a sample MX may remain substantially constant during varying the reflection angle $\phi$ from a first value to a second value. In an embodiment, the reflection angle $\phi$ may be varied in order to record a first reflectance curve associated with a first sample composition, the composition of the sample may be changed, and the reflection angle $\phi$ may be varied in order to record a second reflectance curve associated with a second sample composition. The control unit CNT1 may be arranged to control or monitor the angle $\phi$. The control unit CNT1 may send and/or receive a position signal $SNG_2$, $SNG_3$. The control unit CNT1 may send one or more position signals $SNG_2$, $SNG_3$ to one or more actuators 320, 330 and/or the control unit CNT1 may receive position signals $SNG_2$, $SNG_3$ from one or more position sensors.

The control unit CNT1 may optionally modulate the light source 250. In particular, the intensity of the input beam B0 may be modulated e.g. in order to improve signal-to-noise ratio of the detector signal $SNG_1$. The intensity of the input beam B0 may be modulated e.g. by sending a signal $SNG_5$ to the light source 250.

The apparatus 500 may optionally comprise one or more fluid-confining walls 190. The one or more walls 190, the conductive layer 120, and optionally also the substrate 110 may together form a sample cell 100 for containing a sample MX. In an embodiment, the sample MX may comprise a functional layer AF1, an amount of analyte molecules M1 bound to the functional layer, and bulk material in a substantially liquid state. The sample cell 100 may be e.g. a cuvette.

The apparatus 500 may optionally comprise a composition adjusting unit 410 for changing the composition of a sample MX. The composition adjusting unit 410 may comprise e.g. one or more valves, one or more pumps, and one or more branching elements (e.g. a T-piece) for providing a sample MX, which has a desired composition. For example, the composition adjusting unit 410 may be arranged to provide a sample MX by mixing two or more components COMP1, COMP2. For example, the composition adjusting unit 410 may be arranged to provide a first sample MX which has a first composition during a first time period, and to provide a second sample MX which has a second different composition during a second time period. For example, the composition adjusting unit 410 may be arranged to provide a first sample MX by guiding a first component COMP1 to the cell 100 during a first time period, and to provide a second sample MX by guiding a second component COMP2 to the cell 100 during a second time period. The operation of the composition adjusting unit 410 may be controlled e.g. by sending a control signal $SNG_4$ to the composition adjusting unit 410. The composition adjusting unit 410 may comprise e.g. a syringe pump or a peristaltic pump for injecting a second substance COMP2 into a first substance COMP1 during a first time period, wherein the injection of the second substance COMP2 may be stopped at the end of the first time period. In an embodiment, the sample MX provided by the composition adjusting unit 410 may be a mixture of the substances COMP1, COMP2 during the first time period, and the sample MX provided by the composition adjusting unit 410 may substantially consist of the first substance COMP1 during a second time period.

The apparatus 500 may optionally comprise a temperature control unit 420 for controlling the temperature of the sample MX. The temperature control unit 420 may comprise e.g. a heater and/or a cooler. The operation of the temperature control unit 420 may be controlled e.g. by a signal $SNG_6$. The control unit CNT1 may be arranged to provide the signal $SNG_6$.

The apparatus 500 may comprise a memory MEM1 for storing operating parameters PAR1. The operating parameters PAR1 may comprise e.g. coefficients A, B, C of a regression function $f_1$ (see equation (6b)). The apparatus 500 may comprise a memory MEM2 for storing measured data DATA1. The apparatus 500 may comprise a memory MEM3 for storing computer program PROG1. The computer program PROG1 may be configured to, when executed by at least one processor CNT1, cause the apparatus 500 to measure data and process data.

For example, the computer program PROG1 may be configured to, when executed by at least one processor CNT1, cause the apparatus 500 to perform at least the following:

measure a first surface plasmon resonance angle value of a sample region when the sample region (REG1) has a first surface concentration of an analyte and first bulk composition, measure a first critical angle value of the sample region, measure a second surface plasmon resonance angle value of the sample region when the sample region has a second surface concentration of an analyte and second bulk composition, measure a second critical angle value of the sample, and determine an indicator value indicative of the change of the surface concentration wherein the indicator value is determined from the second surface plasmon resonance angle value by compensating an effect of the bulk composition, and wherein the magnitude of said effect is determined by using the second critical angle value.

The directions of the beams B0, B1 outside the substrate 110 may be different from the directions of the beams B0, B1 outside the substrate 110. The angles φ and φ' specify the direction of the beams B1, B0 inside the substrate 110.

Figure 2A:
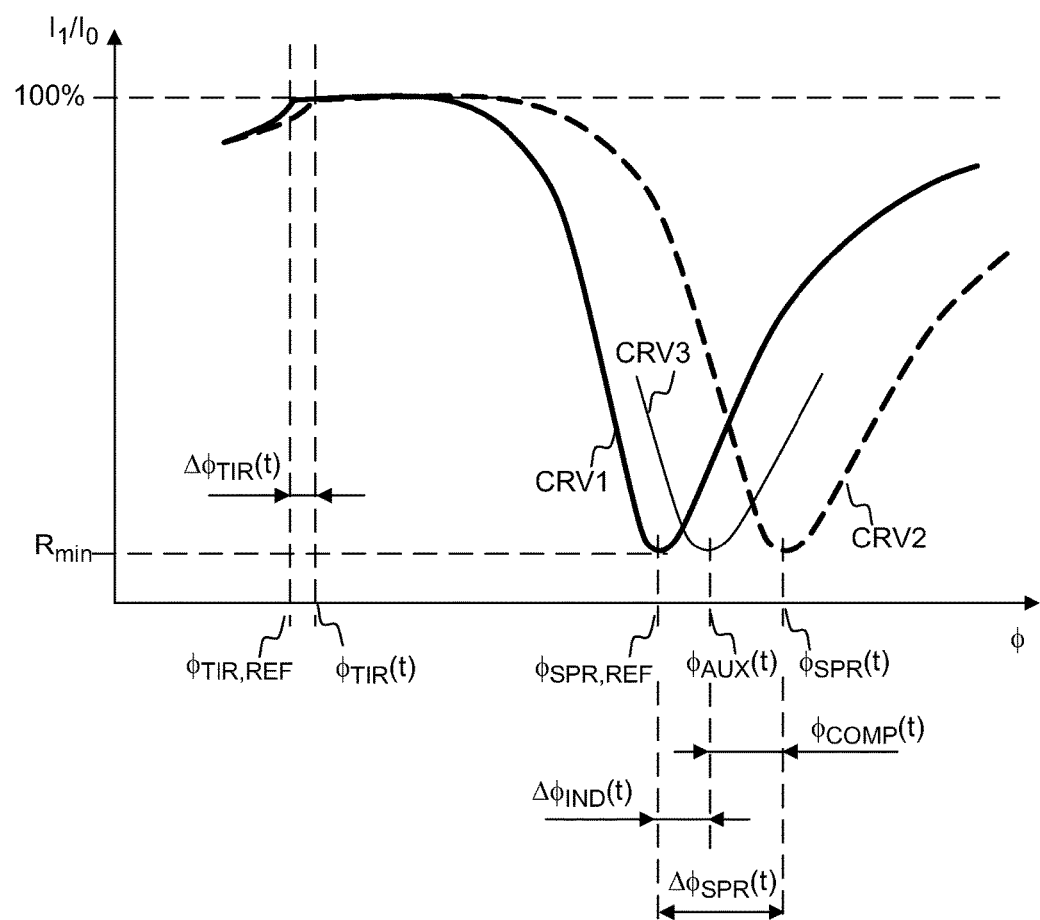
FIG. 2a shows, by way of example, reflectance of the sample region as a function of reflection angle.
Figure 2B:
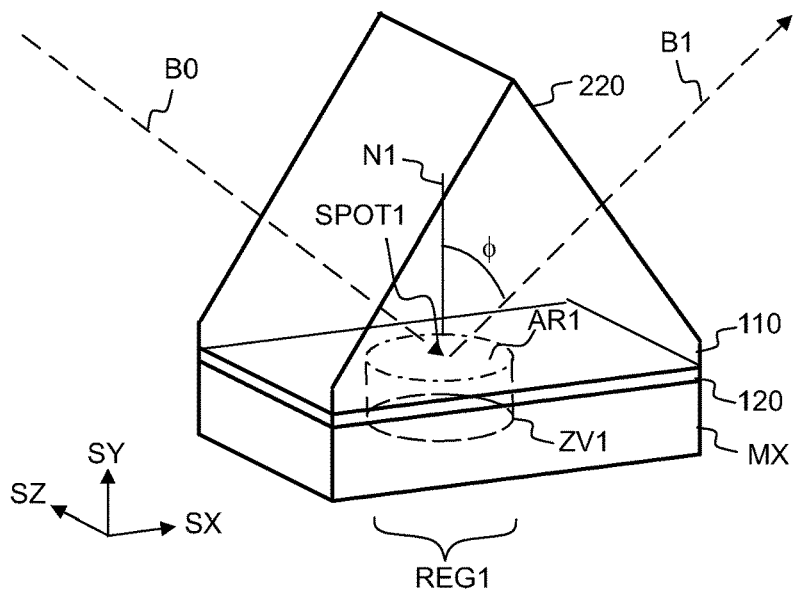
FIG. 2b shows, by way of example, in a three dimensional view, the sample region.

SX, SY and SZ denote orthogonal directions (see FIG. 2b). The substantially planar surface of the conductive layer 120 may be in a plane defined by the directions SX and SZ.

Figure 1B:
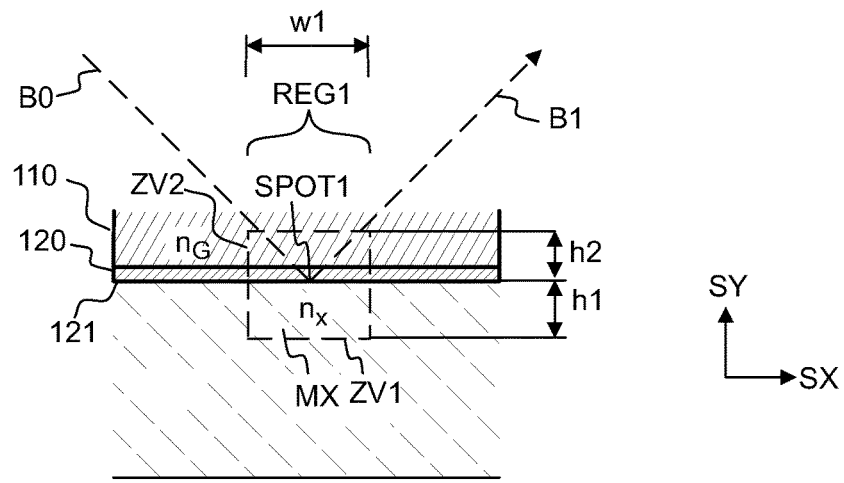
FIG. 1b shows, by way of example, in a cross sectional view, a sample region of the surface plasmon resonance sensor.

Referring to FIG. 1b, the sensor 200 may be arranged to analyze a sample MX contained in a sample volume ZV1 of a sample region REG1. The input beam B0 may impinge on the conductive layer 120 so that the beam B1 may be reflected from the sample region REG1 of the sensor 200. The sample region REG1 may comprise a first portion ZV1 and a second portion ZV2. The first portion may also be called e.g. as the sensor volume. The sample volume ZV1 may contain a sample MX.

The second portion ZV2 of the sample region REG1 may comprise two or more material layers. A first material layer may consist of the material of the substrate 110, and a second material layer may consist of the material of the conductive layer 120. For example, the second portion ZV2 may comprise a first layer which consists of glass, and a second layer, which consists of a metal, e.g. gold.

The sample volume ZV1 may have a width w1. The input beam B0 may form an illuminated spot on the conductive layer 120. In an embodiment, the width w1 of the sample volume ZV1 may be defined by the width of the illuminated spot. The center of the input beam B0 may impinge on the conductive layer 120 at a position SPOT1.

The substrate 110 may have a refractive index $n_G$, and the sample MX may have a refractive index $n_x$. The refractive index $n_G$ of the substrate 110 may be greater than the refractive index $n_x$ of the sample volume ZV1 in order to enable total internal reflection (TIR).

The input beam B0 impinging on the sample region REG1 may form an evanescent wave, which penetrates into the sample MX. The intensity $I_1$ of the reflected beam B1 may depend on the interaction between the evanescent wave and the sample MX. The intensity of the evanescent wave may decay exponentially such that material located outside the sample volume ZV1 does not have an effect on the intensity $I_1$ of the reflected beam B1. The thickness h1 of the sample volume ZV1 may depend on the penetration depth of the evanescent wave. The thickness h1 may be e.g. smaller than or equal to the wavelength $\lambda_1$ of the reflected beam B1. The second portion ZV2 may have a thickness h2.

Figure 1C:
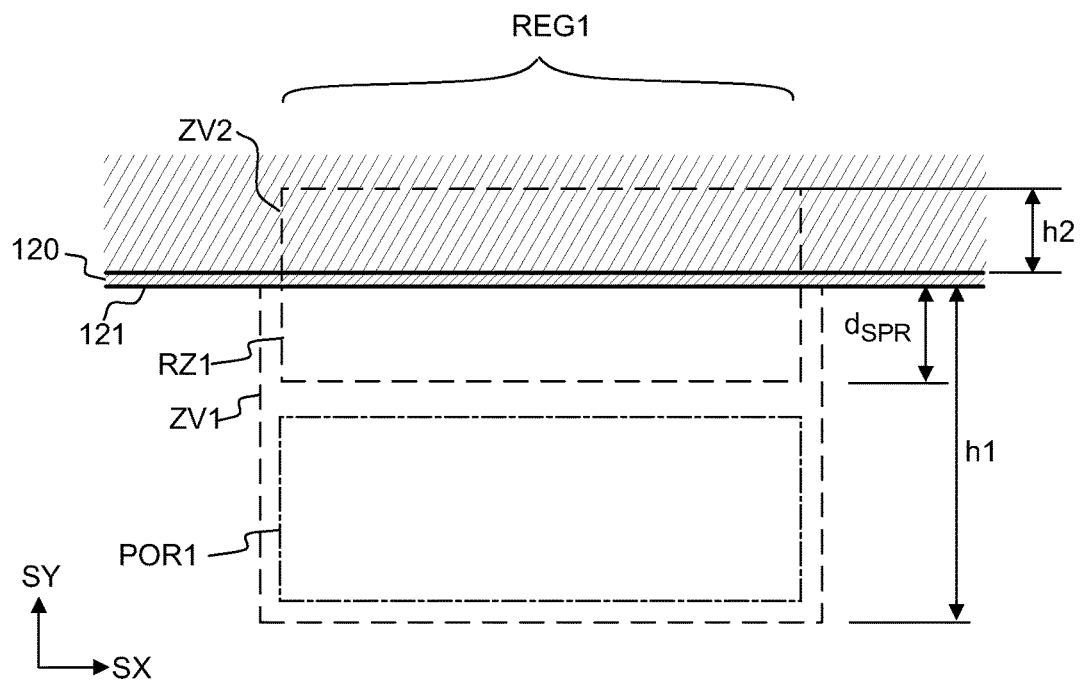
FIG. 1c shows, by way of example, in a cross sectional view, a sample volume and a resonance volume of the sample region.

Referring to FIG. 1c, the sample MX contained in the sample region REG1 may be analyzed by using total internal reflection and by using surface plasmon resonance. The sample volume ZV1 may comprise a resonance volume RZ1. The resonance volume RZ1 may comprise a sample MX. The sample volume ZV1 may have a height h1, and the resonance volume RZ1 may have a height $d_{SPR}$. The height h1 of the sample volume ZV1 may be determined by the penetration depth of the evanescent field caused by the total internal reflection. The penetration depth thin may refer to the depth where the intensity falls to a value, which is 36.7% (=1/e) of its value at the interface 121.

The height $d_{SPR}$ of the resonance volume RZ1 may be determined by the effective penetration depth of the surface plasmon polaritons. The height $d_{SPR}$ of the resonance volume RZ1 may be smaller than the height h1 of the sample volume ZV1, due to the spatial confinement of the surface plasmon polaritons.

The sample volume ZV1 may have a portion POR1, which is located beneath the resonance volume RZ1. The portion POR1 may be called e.g. as the bulk portion.

FIG. 2a shows a first reflectivity curves CRV1 for a first sample, and a second reflectivity curve CRV2 for a second sample. The first sample may be changed into the second sample e.g. in order to study surface phenomena which take place on a functional layer of the sensor 200.

The first reflectivity curve CRV1 may be measured at a reference time $t_{REF}$ when the sample volume ZV1 contains the first sample, and the second reflectivity curve CRV2 may be measured at a second time t when the sample volume ZV1 contains the second sample.

$I_0$ may denote the spectral intensity of the input beam B0 at the wavelength $\lambda_1$, and $I_1$ may denote the spectral intensity of the reflected p-polarized beam B1 at the same wavelength $\lambda_1$. The reflectivity may be indicated by the ratio $I_1/I_0$. The ratio $I_1/I_0$ may depend on the reflection angle φ. The curves CRV1, CRV2 show the reflectivity $I_1/I_0$ as the function of the reflection angle φ.

The critical angle may have a first critical angle value $\phi_{TIR,REF}$ when the sample volume ZV1 contains the first sample. The critical angle may have a second critical angle value $\phi_{TIR}(t)$ when the sample volume ZV1 contains the second sample.

The criterion for total internal reflection (TIR) may be fulfilled when the reflection angle φ is greater than or equal to the critical angle $\phi_{TIR}$. The smallest angle φ, which causes total internal reflection is called as the critical angle $\phi_{TIR}$. The critical angle $\phi_{TIR}$ may depend on the refractive index values $n_x$ and $n_G$ according to the following equation:

$$\sin\phi_{TIR} = \frac{n_x}{n_G} \quad (1a)$$

$n_G$ denotes the refractive index of the substrate 110. $n_x$ denotes the (average) refractive index of the sample volume ZV1. The refractive index $n_x$ may represent a spatially averaged refractive index of the sample contained in the sample volume ZV1. The refractive index $n_x$ may depend on the refractive index of one or more material layers, which are attached to the surface 121, and the refractive index $n_x$ may also depend on the refractive index of materials which are located within the sample volume ZV1 but which are not attached to the surface 121. The refractive index $n_x$ may depend on the bulk properties of the sample, but also on the surface concentration $c_{M1,SRF}$ of an analyte M1 bound to the surface 121.

$n_x(t)$ may denote the average refractive index of the sample volume ZV1 at the time t, and $\phi_{TIR}(t)$ may denote the critical angle at said time t. The critical angle $\phi_{TIR}(t)$ at the time t may depend on the refractive index values $n_x(t)$ and $n_G$ according to the following equation:

$$\sin\phi_{TIR}(t) = \frac{n_x(t)}{n_G} \quad (1b)$$

$n_x(t_{REF})$ may denote the average refractive index of the sample volume ZV1 at the reference time $t_{REF}$, and $\phi_{TIR,REF}$ may denote the critical angle at the reference time $t_{REF}$. The critical angle $\phi_{TIR,REF}$ at the reference time $t_{REF}$ may be determined by the following equation:

$$\sin\phi_{TIR,REF} = \frac{n_x(t_{REF})}{n_G} \quad (1c)$$

The spectral reflectivity $I_1/I_0$ may have a local minimum caused by surface plasmon resonance. The minimum reflectivity $I_1/I_0$ may be attained at an angular position, which may be called e.g. as the surface plasmon resonance angle $\phi_{SPR}$.

The surface plasmon resonance angle $\phi_{SPR}$ may depend on the optical properties of the resonance volume RZ1 e.g. according to equation (2a) or (2b):

$$\sin\phi_{SPR} = \frac{1}{n_G}\sqrt{\frac{\varepsilon_2 \cdot \varepsilon_x}{\varepsilon_2 + \varepsilon_x}} \quad (2a)$$

$$\phi_{SPR} = \arcsin\left[\frac{1}{n_G}\sqrt{\frac{\varepsilon_2 \cdot \varepsilon_x}{\varepsilon_2 + \varepsilon_x}}\right] \quad (2b)$$

where $n_G$ denotes the refractive index of the substrate 110, $\varepsilon_2$ denotes the real part of the dielectric permittivity of the conductive layer 120, and $\varepsilon_x$ denotes the dielectric permittivity of the sample MX contained in the resonance volume RZ1.

The surface plasmon resonance angle $\phi_{SPR}$ may be related to the dielectric permittivity $\varepsilon_x$ of the sample MX e.g. by using the equation (2a) or (2b).

The surface plasmon resonance may cause increased absorption of light when the reflection angle $\phi$ is substantially equal to the surface plasmon resonance angle $\phi_{SPR}$. Consequently, the intensity $I_1$ of the reflected light B1 may decrease when the surface plasmon resonance exists, and the surface plasmon resonance may give rise to the local minimum in the angular reflectivity $I_1(\phi)/I_0$ at the surface plasmon resonance angle $\phi_{SPR}$.

A change in the resonance condition may be related to a change of dielectric permittivity in the resonance volume RZ1. For example, accumulation of a nanoscale film on the surface 121 may be monitored by detecting a change in the resonance condition.

$\varepsilon_x(t)$ may denote the dielectric permittivity of a sample contained in the resonance volume RZ1 at a time t. $\phi_{SPR}(t)$ may denote the surface plasmon resonance angle at the time t.

$$\sin\phi_{SPR}(t) = \frac{1}{n_G}\sqrt{\frac{\varepsilon_2 \cdot \varepsilon_x(t)}{\varepsilon_2 + \varepsilon_x(t)}} \quad (2c)$$

$$\phi_{SPR}(t) = \arcsin\left[\frac{1}{n_G}\sqrt{\frac{\varepsilon_2 \cdot \varepsilon_x(t)}{\varepsilon_2 + \varepsilon_x(t)}}\right] \quad (2d)$$

The surface plasmon resonance angle $\phi_{SPR}(t)$ at the time t may be related to the dielectric permittivity $\varepsilon_x(t)$ of the sample e.g. by using the equation (2c) or (2d).

$\varepsilon_x(t_{REF})$ may denote the dielectric permittivity of a sample contained in the resonance volume RZ1 at the reference time $t_{REF}$. $\phi_{SPR,REF}$ may denote the surface plasmon resonance angle at the reference time t.

$$\sin\phi_{SPR,REF} = \frac{1}{n_G}\sqrt{\frac{\varepsilon_2 \cdot \varepsilon_x(t_{REF})}{\varepsilon_2 + \varepsilon_x(t_{REF})}} \quad (2e)$$

$$\phi_{SPR,REF} = \arcsin\left[\frac{1}{n_G}\sqrt{\frac{\varepsilon_2 \cdot \varepsilon_x(t_{REF})}{\varepsilon_2 + \varepsilon_x(t_{REF})}}\right] \quad (2f)$$

The surface plasmon resonance angle $\phi_{SPR,REF}$ at the reference time $t_{REF}$ may be related to the dielectric permittivity $\varepsilon_x(t_{REF})$ of the sample e.g. by using the equation (2e) or (2f).

A first surface plasmon resonance angle $\phi_{SPR,REF}$ may be determined from the first reflectivity curve CRV1, which may be measured when the sample volume ZV1 contains a first sample. $R_{min}$ denotes the minimum value of the first reflectivity curve CRV1.

A second surface plasmon resonance angle $\phi_{SPR}(t)$ may be determined from the second reflectivity curve CRV2, which may be measured when the sample volume ZV1 contains a second sample.

A reference critical angle $\phi_{TIR,REF}$ may be determined from the first reflectivity curve CRV1, which may be measured at a reference time $t_{RER}$ when the sample volume ZV1 contains the first sample.

A critical angle $\phi_{TIR}(t)$ may be determined from the second reflectivity curve CRV2, which may be measured at a time t when the sample volume ZV1 contains the second sample.

The difference $\phi_{TIR}(t)-\phi_{TIR,REF}$ may indicate a change, which takes place in the sample volume ZV1. The difference $\phi_{SPR}(t)-\phi_{SPR,REF}$ may indicate a change, which takes place in the resonance volume RZ1. The penetration depth of the surface plasmon polaritons may be smaller than the penetration depth thin of the evanescent wave caused by the total internal reflection. The change $\phi_{SPR}(t)-\phi_{SPR,REF}$ of the surface plasmon resonance angle may be substantially insensitive to a change of composition, which takes place outside the resonance volume RZ1. The change $\phi_{SPR}(t)-\phi_{SPR,REF}$ of the surface plasmon resonance angle may be substantially insensitive to a change of bulk composition, which takes place in the bulk portion POR1 of the sample volume ZV1 outside the resonance volume RZ1 (see FIG. 1c).

The difference $\phi_{TIR}(t)-\phi_{TIR,REF}$ may indicate a change, which takes place in the sample volume ZV1, even if said change would take place outside the resonance volume RZ1. The difference $\phi_{TIR}(t)-\phi_{TIR,REF}$ may be substantially insensitive to a change of surface concentration $c_{M1,SRF}$ in the resonance volume RZ1, within the distance $d_{SPR}$ from the conductive layer 120.

The difference $\phi_{TIR}(t)-\phi_{TIR,REF}$ may primarily indicate a change of bulk properties within the sample volume ZV1, wherein the difference $\phi_{SPR}(t)-\phi_{SPR,REF}$ may primarily indicate a change of surface properties close to the surface 121. The difference $\phi_{TIR}(t)-\phi_{TIR,REF}$ may be used as an indicator for a change of bulk properties within the sample volume ZV1, wherein the difference $\phi_{SPR}(t)-\phi_{SPR,REF}$ may be used as an indicator for a change of surface properties. However, the selectivity of said indicators may be less than 100%. For example, a change of composition close to the surface 121 may also have an effect on the difference $\phi_{TIR}(t)-\phi_{TIR,REF}$, and/or a change of bulk properties may also have an effect on the difference $\phi_{SPR}(t)-\phi_{SPR,REF}$.

When using a change of the surface plasmon resonance angle $\phi_{SPR}$ as an indicator for a surface phenomenon, the selectivity of said indicator may be improved by using an auxiliary angle $\phi_{AUX}$. The auxiliary angle $\phi_{AUX}$ may be defined e.g. by the following equation:

$$\phi_{AUX}(t)=\phi_{SPR}(t)-\phi_{COMP}(t) \quad (3)$$

where $\phi_{COMP}(t)$ denotes a compensating angle value. The auxiliary angle $\phi_{AUX}(t)$ may be interpreted to be a surface plasmon resonance angle $\phi_{SPR}$ in a hypothetical situation where only the surface properties have been changed without changing the bulk properties of the sample volume ZV1. The curve CRV3 shows reflectivity in case of said hypothetical situation. The compensating angle value $\phi_{COMP}(t)$ may also be called e.g. as a bulk effect value.

The auxiliary angle $\phi_{AUX}$ may be used as an indicator value indicative of the change of the surface concentration $c_{M1,SRF}$ of an analyte, wherein the indicator value $\phi_{AUX}(t)$ may be determined from the surface plasmon resonance angle value $\phi_{SPR}(t)$ by compensating an effect of the bulk composition, and wherein the magnitude $\phi_{COMP}$ of said effect may be determined by using the critical angle value ($\phi_{TIR}(t)$).

A difference $\phi_{AUX}(t)-\phi_{SPR,REF}$ between the auxiliary angle $\phi_{AUX}(t)$ and the reference surface plasmon resonance angle $\phi_{SPR,REF}$ may be determined by using the compensating angle value $\phi_{COMP}(t)$:

$$\phi_{AUX}(t)-\phi_{SPR,REF}=\phi_{SPR}(t)-\phi_{COMP}(t)-\phi_{SPR,REF} \quad (4a)$$

When studying binding of an analyte to an active layer of the sample region REG1, the auxiliary angle $\phi_{AUX}(t)$ may be a more selectively dependent on the surface concentration of a substance M1 than the surface plasmon resonance angle $\phi_{SPR}(t)$. The auxiliary angle $\phi_{AUX}(t)$ may be indicative of the surface concentration $c_{M1,SRF}$ of the analyte M1 at the sample region REG1. $\phi_{AUX}(t_{REF})$ may denote the auxiliary angle value $\phi_{COMP}(t)$ at a reference time $t_{REF}$. When used together with the reference value $\phi_{AUX}(t_{REF})$, the auxiliary angle $\phi_{AUX}(t)$ may be indicative of a change of surface concentration $c_{M1,SRF}$ of the analyte M1 at the sample region REG1. When compared with the reference value $\phi_{AUX}(t_{REF})$, the auxiliary angle $\phi_{AUX}(t)$ may be indicative of a change of surface concentration $c_{M1,SRF}$ of the analyte M1 at the sample region REG1. The difference $\phi_{SPR}(t)-\phi_{SPR,REF}$ may be indicative of a change of surface concentration the analyte. The difference $\phi_{AUX}(t)-\phi_{AUX}(t_{REF})$ may indicate a change of surface concentration more selectively than the difference $\phi_{SPR}(t)-\phi_{SPR,REF}$.

The difference $\phi_{AUX}(t)-\phi_{SPR,REF}$ may be called e.g. as a compensated indicator value $\Delta\phi_{IND}(t)$.

$$\Delta\phi_{IND}(t)=\phi_{AUX}(t)-\phi_{SPR,REF} \quad (4b)$$

$$\Delta\phi_{IND}(t)=\phi_{SPR}(t)-\phi_{COMP}(t)-\phi_{SPR,REF} \quad (4c)$$

The difference $\phi_{AUX}(t)-\phi_{SPR,REF}$ may also be indicative of a change of surface concentration of the analyte at the sample region REG1.

The compensating angle value $\phi_{COMP}$ may be determined e.g. by using the following equation:

$$\phi_{COMP}(t) = \arcsin\left[\frac{1}{n_G}\sqrt{\frac{\varepsilon_2 \cdot \varepsilon_x(t)}{\varepsilon_2 + \varepsilon_x(t)}}\right] \quad (5a)$$

where $n_G$ denotes the refractive index of the substrate 110, $\varepsilon_2$ denotes the real part of the dielectric permittivity of the conductive layer 120, and $\varepsilon_x(t)$ denotes a dielectric permittivity value estimated from the critical angle $\phi_{TIR}(t)$.

The permittivity value $\varepsilon_x(t)$ may be calculated e.g. by using the following equation:

$$\varepsilon_x(t)=n_G^2 \sin^2 \phi_{TIR}(t) \quad (5b)$$

The relationship between the compensating angle value $\phi_{COMP}(t)$ and the critical angle $\phi_{TIR}(t)$ may also be expressed e.g. by a compensating angle function $f_1(\phi_{TIR})$:

$$\phi_{COMP}(t)=f_1(\phi_{TIR}(t)) \quad (6a)$$

The compensating angle function $f_1(\phi_{TIR})$ may also be called e.g. as a regression function. The compensating angle function $f_1$ may be determined e.g. by experimental calibration measurements and/or by calculating a plurality of data points ($\phi_{COMP},\phi_{TIR}$) from the equation (5a), and by fitting a regression function $f_1$ to the calculated data points.

The compensating angle function $f_1(\phi_{TIR})$ may be determined e.g. by:
- measuring a first auxiliary surface plasmon resonance angle value ($\phi_{SPR1}$),
- measuring a first auxiliary critical angle value ($\phi_{TIR1}$),
- changing the bulk composition (e.g. by changing a bulk concentration $c_{M3}$),
- measuring a second auxiliary surface plasmon resonance angle value ($\phi_{SPR1}$) of a sample region (REG1),
- measuring a second auxiliary critical angle value ($\phi_{TIR2}$) of the sample region (REG1),
- calculating a first difference ($\Delta\phi_{SPR12}$) between the first and the second auxiliary surface plasmon resonance angle values,
- calculating a second difference ($\Delta\phi_{TIR12}$) between the first and the second critical angle values, and
- determining at least one parameter of the compensating angle function from the first difference ($\Delta\phi_{SPR12}$) and the second difference ($\Delta\phi_{TIR12}$).

Figure 7A:
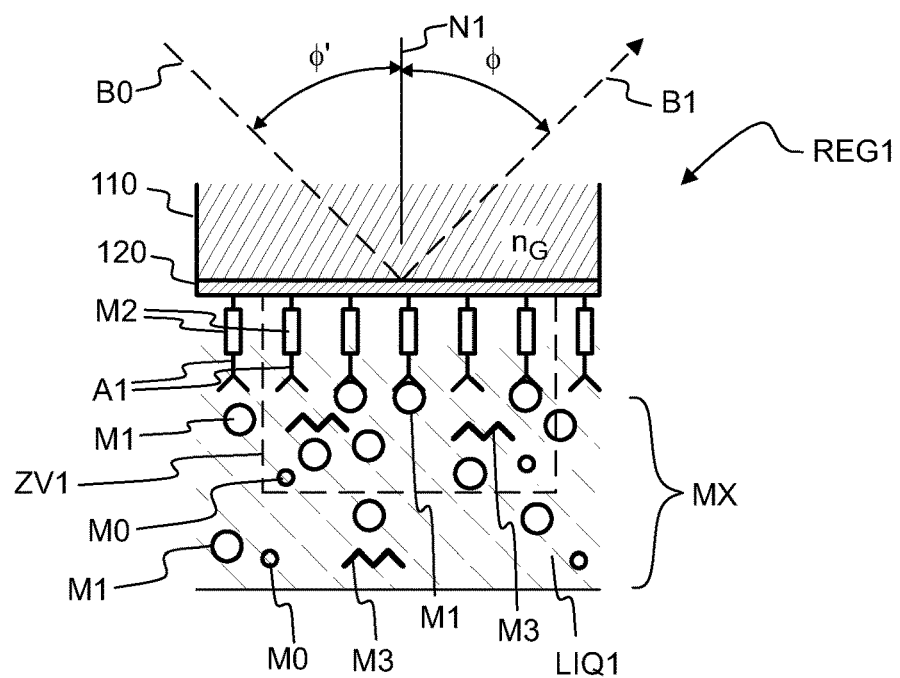
FIG. 7a shows, by way of example, in a cross sectional view, the sample region during an adsorption test.
Figure 7B:
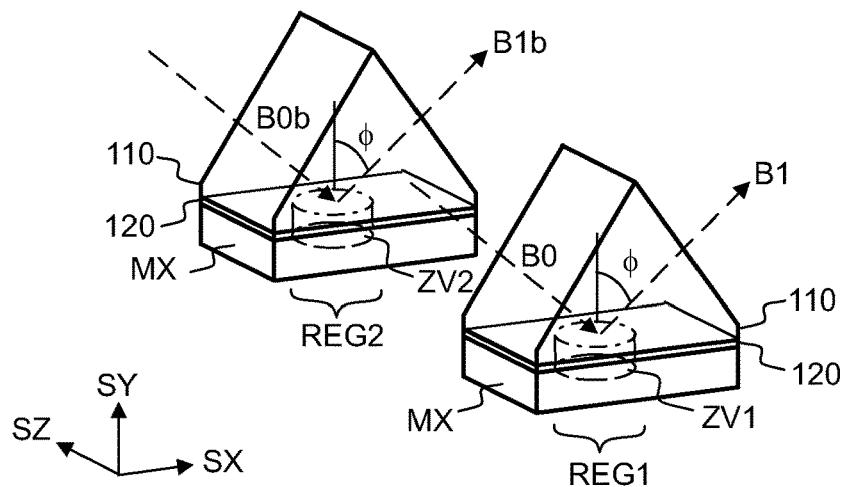
FIG. 7b shows, by way of example, in a three dimensional view, a first sample region and a second sample region.
Figure 7C:
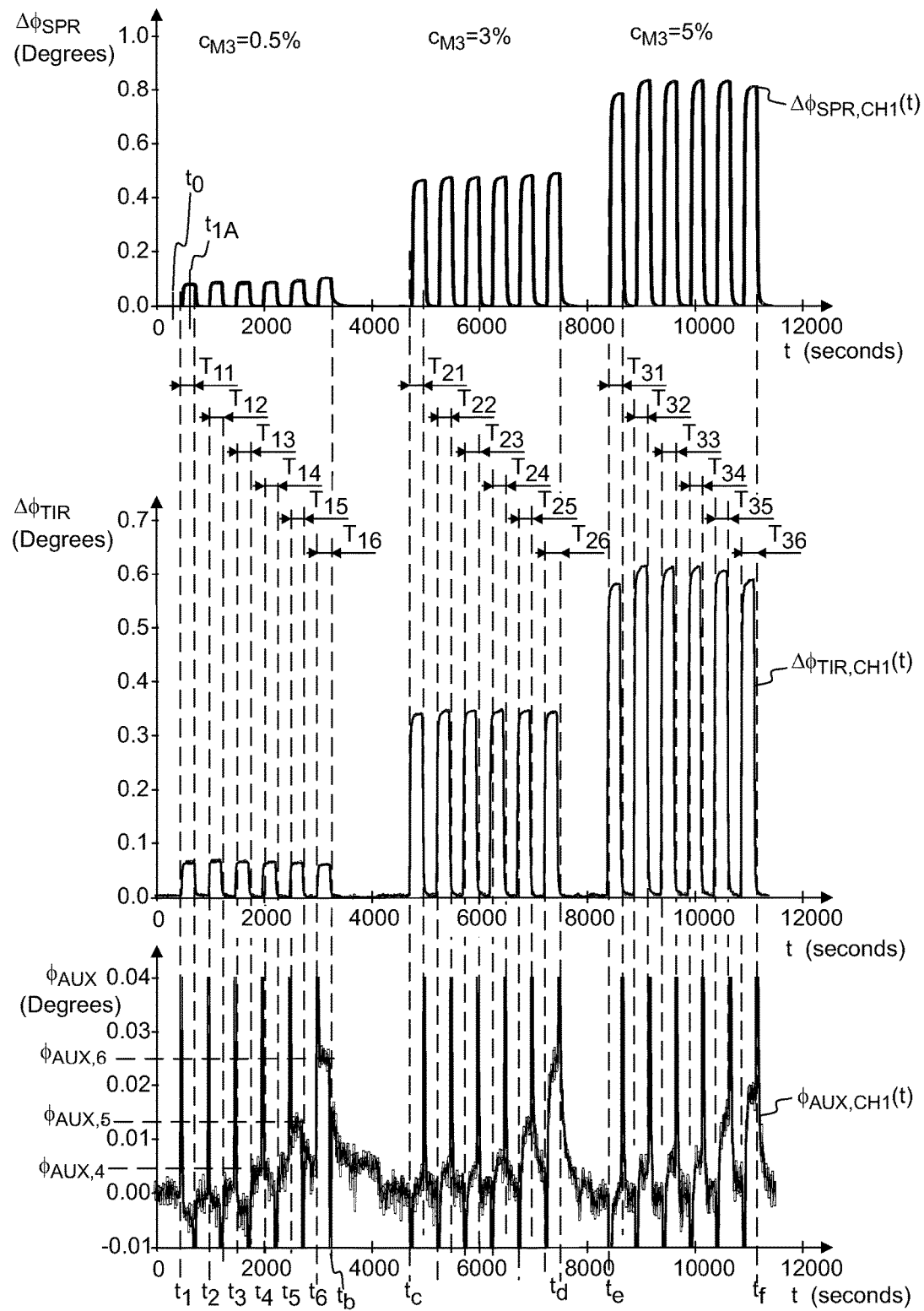
FIG. 7c shows, by way of example, temporal evolution of angle values during a first adsorption test.
Figure 7D:
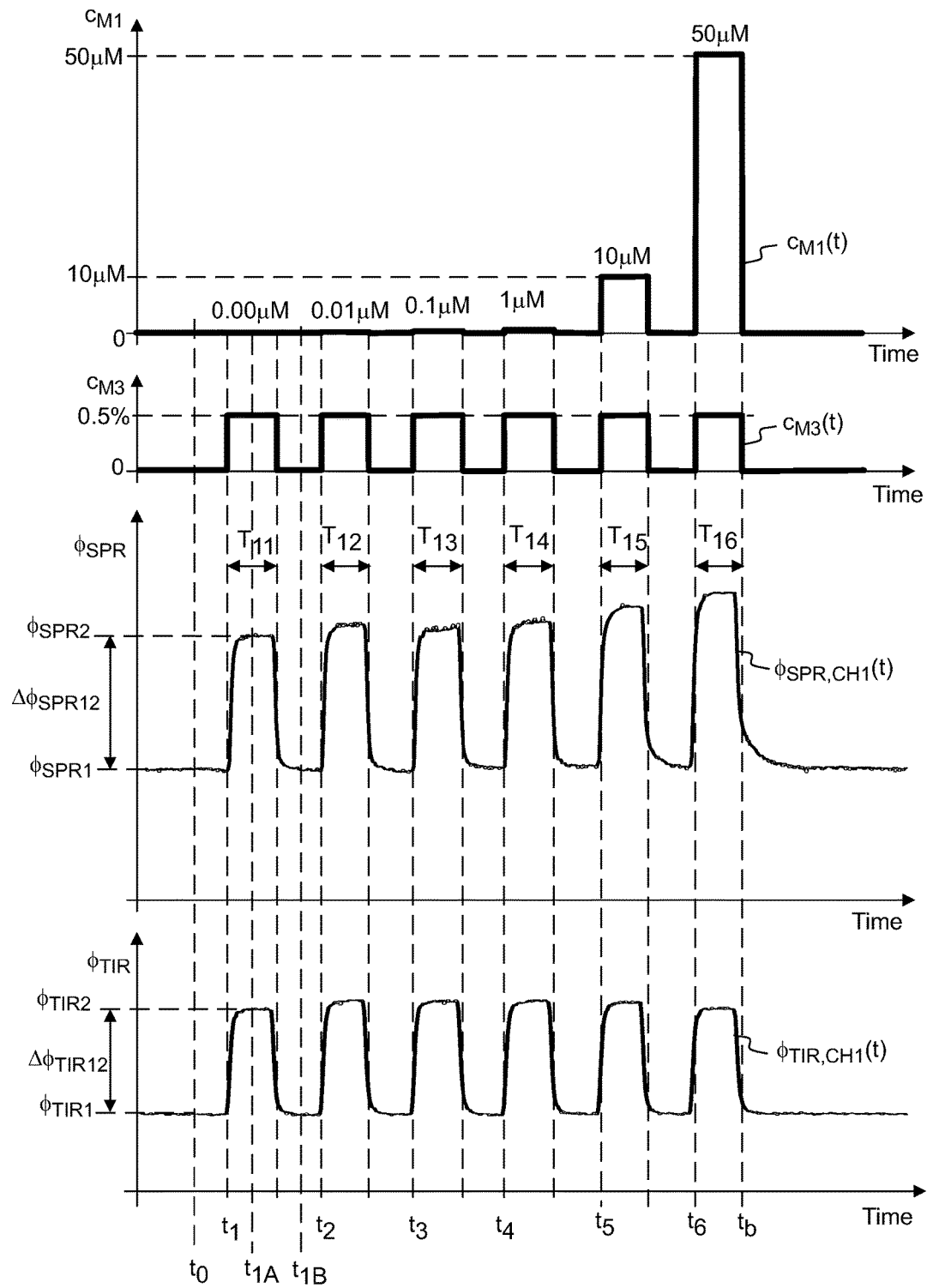
FIG. 7d shows, by way of example, temporal evolution of concentrations and angle values during a first part of the first adsorption test of FIG. 7c.

The auxiliary angle values are shown e.g. in FIG. 7d.

The first auxiliary surface plasmon resonance angle value ($\phi_{SPR1}$) and the first auxiliary critical angle value ($\phi_{TIR1}$) may be measured when the sample volume (ZV1) of a sample region (REG1) comprises a first auxiliary sample, and the second auxiliary surface plasmon resonance angle value ($\phi_{SPR2}$) and the second auxiliary critical angle value ($\phi_{TIR2}$) may be measured when the sample volume (ZV1) comprises a second auxiliary sample.

The first auxiliary surface plasmon resonance angle value ($\phi_{SPR1}$) and the first auxiliary critical angle value ($\phi_{TIR1}$) may be measured when the sample volume (ZV1) of a sample region (REG1) comprises a first concentration ($c_{M3}$) of a substance (M3), and the second auxiliary surface plasmon resonance angle value ($\phi_{SPR2}$) and the second auxiliary critical angle value ($\phi_{TIR2}$) may be measured when the sample volume (ZV1) comprises a second different concentration ($c_{M3}$) of said substance (M3).

The compensating angle function $f_1$ may be determined by:
- providing a plurality of auxiliary critical angle values ($\phi_{TIR1}$, $\phi_{TIR2}$),
- calculating an auxiliary surface plasmon resonance angle value ($\phi_{SPR1},\phi_{SPR2}$) from each auxiliary critical angle value ($\phi_{TIR1}$, $\phi_{TIR2}$), and
- fitting the compensating angle function ($f_1(\phi_{TIR})$) to the auxiliary surface plasmon resonance angle values ($\phi_{SPR1},\phi_{SPR2}$).

The dielectric permittivity ($\varepsilon_x$) of each sample (MX) may be calculated from an auxiliary critical angle (prim), and an auxiliary surface plasmon resonance angle ($\phi_{SPR1}$) for said sample (MX) may be calculated from the dielectric permittivity ($\varepsilon_x$) of the sample, from the dielectric permittivity ($\varepsilon_2$) of a conductive layer (120), and from the dielectric permittivity ($\varepsilon_G$) of a substrate (110).

The regression function $f_1$ may be e.g. a polynomial function:

$$f_1(\phi_{TIR})=A \cdot (\phi_{TIR})^3 + B \cdot (\phi_{TIR})^2 + C \cdot (\phi_{TIR}) + D \quad (6b)$$

The compensating angle value $\phi_{COMP}(t)$ may be determined e.g. by using the polynomial regression function:

$$\phi_{COMP}(t)=A \cdot (\phi_{TIR})^3 + B \cdot (\phi_{TIR})^2 + C \cdot (\phi_{TIR}) + D \quad (6c)$$

The parameters A, B, C, and D of the function $f_1$ may be determined e.g. by experimental calibration measurements, or by calculating a plurality of data points ($\phi_{TIR},\phi_{COMP}$)

from the equation (5a), and by fitting a polynomial function to the calculated data points. The parameters A, B, C, and D of the function $f_1$ may be determined e.g. by fitting a polynomial function to a plurality of data points ($\phi_{TIR}$, $\phi_{COMP}$) determined by experimental calibration measurements.

The function $f_1$ may be e.g. a n-order polynomial function ($A \cdot (\phi_{TIR})^n + B \cdot (\phi_{TIR})^{n-1} + C \cdot (\phi_{TIR})^{n-2} \ldots$), where the order n is an integer. The order n of the polynomial may be e.g. equal to 1, 2, 3, 4, or 5. The function $f_1$ may be a third order polynomial function. The function $f_1$ may be second order polynomial function, wherein the parameter A may be substantially equal to zero. The function $f_1$ may be a linear function, wherein the parameters A and B may be substantially equal to zero. In an embodiment, the regression function $f_1$ may also be e.g. an exponential function, i.e. $f_1(\phi_{TIR}) = \alpha \cdot e^{\beta \cdot \phi_{TIR}} + \gamma$, where the parameters $\alpha$, $\beta$, $\gamma$ may be determined by fitting the regression function $f_1(\phi_{TIR})$ to the data points, which have been determined experimentally and/or from the equation (5a).

Thus, the auxiliary angle $\phi_{AUX}$ may be determined e.g. by using a polynomial regression equation:

$$\phi_{AUX}(t) = \phi_{SPR}(t) - (A \cdot (\phi_{TIR}(t))^3 + B \cdot (\phi_{TIR}(t))^2 + C \cdot (\phi_{TIR}(t)) + D) \quad (6d)$$

In an embodiment, the auxiliary angle $\phi_{AUX}$ may be determined from a surface plasmon resonance angle $\phi_{SPR}$ and from a critical angle $\phi_{TIR}$ also in a situation where the surface plasmon resonance angle $\phi_{SPR}$ and the critical angle $\phi_{TIR}$ are not measured at the same time. In that case, the auxiliary angle $\phi_{AUX}$ may be calculated e.g. by using equation (6e):

$$\phi_{AUX} = \phi_{SPR} - (A \cdot (\phi_{TIR})^3 + B \cdot (\phi_{TIR})^2 + C \cdot (\phi_{TIR}) + D) \quad (6e)$$

For example, an auxiliary angle $\phi_{AUX}$ may be determined from a surface plasmon resonance angle $\phi_{SPR}(t)$ which has been measured at a time t, and from a critical angle $\phi_{TIR}(t')$ which has been measured from the same sample region REG1 at a different time t', wherein the different time t' may be before or after said time t. $\Delta t_{LAG}$ may denote a time lag between measuring the surface plasmon resonance angle value $\phi_{SPR}(t)$ and the critical angle value $\phi_{TIR}(t')$. Consequently:

$$t' = t + \Delta t_{LAG} \quad (6f)$$

In that case, the auxiliary angle $\phi_{AUX}$ may be calculated e.g. by using equation (6g):

$$\phi_{AUX}(t) = \phi_{SPR}(t) - (A \cdot (\phi_{TIR}(t'))^3 + B \cdot (\phi_{TIR}(t'))^2 + C \cdot (\phi_{TIR}(t')) + D) \quad (6g)$$

FIG. 2b shows, in a three dimensional view, reflection of the output beam B1 from the sample region REG1. The input beam B0 and the reflected beam B1 impinging on the detector 210 may together define the sample volume ZV1 of the sample region REG1. The sample volume ZV1 may have a projection AR1 on the conductive layer 120. The projection AR1 may also be called as a projected area. The center of the input beam B0 may impinge on the conductive layer 120 at the point SPOT1.

Figure 2C:
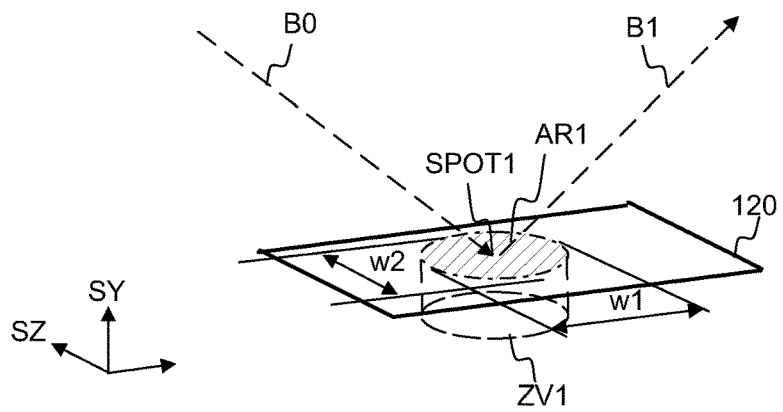
FIG. 2c shows, by way of example, in a three dimensional view, the transverse dimensions of the sample region.

Referring to FIG. 2c, the sample volume ZV1 may have a dimension w1 in the direction SX, and a dimension w2 in the direction SZ. In an embodiment, the surface plasmon resonance angle $\phi_{SPR}$ and the critical angle $\phi_{TIR}$ may be measured by scanning the reflection angle $\phi$ such that the lateral movement of the center of the sample volume ZV1 in the direction SX and/or in the direction SZ is smaller than the dimension w2 of the sample volume ZV1.

Figure 2D:
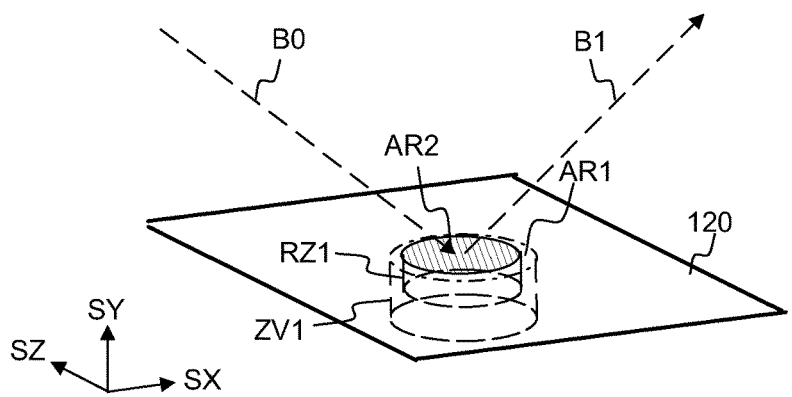
FIG. 2d shows, by way of example, in a three dimensional view, the projection of a sample volume and the projection of a resonance volume.

FIG. 2d shows the projection AR1 of the sample volume ZV1 on the conductive layer 120, and the projection AR2 of the resonance volume RZ1 on the conductive layer 120. The measured surface plasmon resonance angle value $\phi_{SPR}(t)$ may depend on the surface concentration of a substance M1 in the vicinity of the projection AR2, and the measured critical angle value $\phi_{TIR}(t)$ may depend on the bulk composition in the vicinity of the projection AR1. The projection AR1 may overlap the projection AR2 in order to effectively compensate the effect of the bulk composition on the measured surface plasmon resonance angle value $\phi_{SPR}(t)$. The projection AR1 may at least partly overlap the projection AR2. The projection AR1 may completely overlap the projection AR2. The center of the projection AR1 may spatially coincide with the center of the projection AR2.

The apparatus 500 may be arranged to measure a surface plasmon resonance angle value $\phi_{SPR}(t)$ and a critical angle value $\phi_{TIR}(t)$ by monitoring light B1 reflected by the sample region REG1 such that the measured surface plasmon resonance angle value $\phi_{SPR}(t)$ depends on the dielectric permittivity $\varepsilon_x$ of a sample MX located in the resonance volume RZ1 of the sample region REG1, and such that the measured critical angle value $\phi_{TIR}(t)$ depends on the refractive index $n_x$ of a sample MX located in a sample volume ZV1 of the sample region REG1, wherein the projection AR1 of the sample volume ZV1 at least partly overlaps the projection AR2 of the resonance volume RZ1.

In an embodiment, the surface plasmon resonance angle $\phi_{SPR}$ and the critical angle $\phi_{TIR}$ may be measured by scanning (i.e. varying) the reflection angle $\phi$ such that the sample volume ZV1 may remain substantially stationary during the scanning.

Referring to FIGS. 3a to 3f, the sample region REG1 may comprise substantially transparent solid material 110, a metal layer 120, and a functional layer AF1, wherein the metal layer 120 may be located between the solid material 110 and the functional layer AF1. The surface of the conductive layer 120 may be at least partially covered with a functional layer AF1. The functional layer AF1 may be directly deposited on the conductive layer 120, or the sample region REG1 may comprise one or more intermediate dielectric layers between the conductive layer 120 and the functional layer AF1.

Figure 3A:
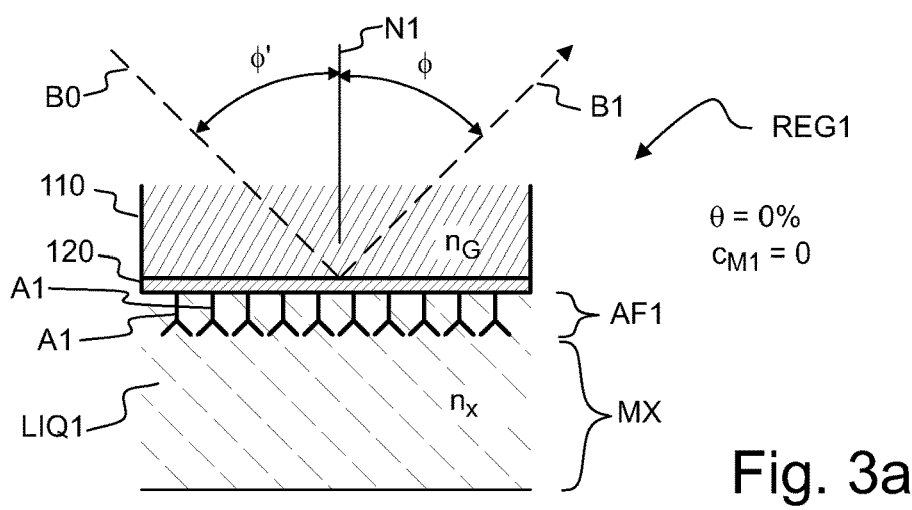
FIG. 3a shows, by way of example, in a cross sectional view, the sample region when the surface coverage is substantially equal to zero.

FIG. 3a shows a situation where the sample MX comprises bulk material LIQ1. The bulk material LIQ1 may be substantially in a liquid state.

In an embodiment, the bulk material LIQ1 may be substantially homogeneous. The concentration $c_{M1}$ of adsorbate molecules M1 in the bulk material LIQ1 may be substantially equal to zero. The surface concentration $c_{AF1,M1}$ of molecules M1 on the functional layer AF1 may be substantially equal to zero. The surface coverage $\theta$ of the functional layer AF1 may be substantially equal to zero.

Figure 3B:
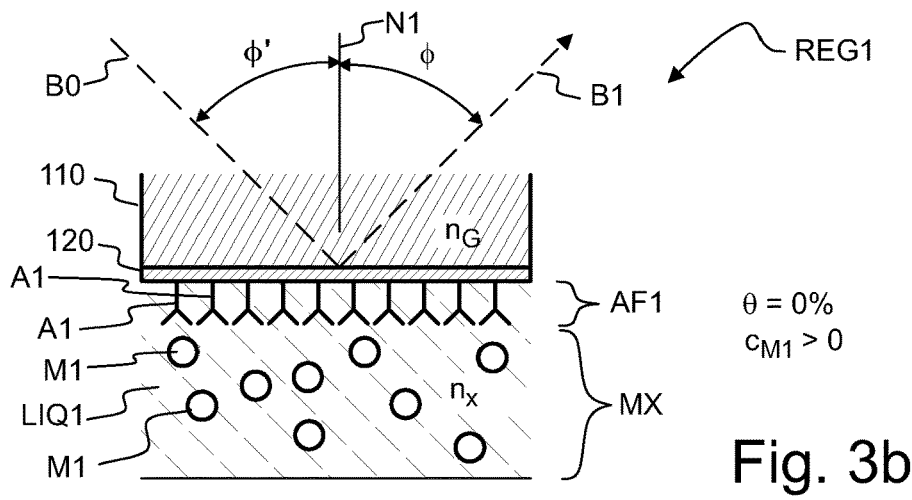
FIG. 3b shows, by way of example, in a cross sectional view, the sample region when the bulk material contains adsorbate molecules.

FIG. 3b shows a situation where the sample MX comprises adsorbate molecules M1 carried in a bulk material LIQ1. The concentration $c_{M1}$ of adsorbate molecules M1 in the bulk material LIQ1 may be greater than zero. Adsorption of the molecules M1 to the active sites A1 of the functional layer AF1 does not take place at an infinite rate. In the beginning of the adsorption, the surface concentration $c_{M1,SRF}$ of molecules M1 on the functional layer AF1 may be substantially equal to zero. In the beginning of the adsorption, the surface coverage $\theta$ of the functional layer AF1 may be substantially equal to zero.

Figure 3C:
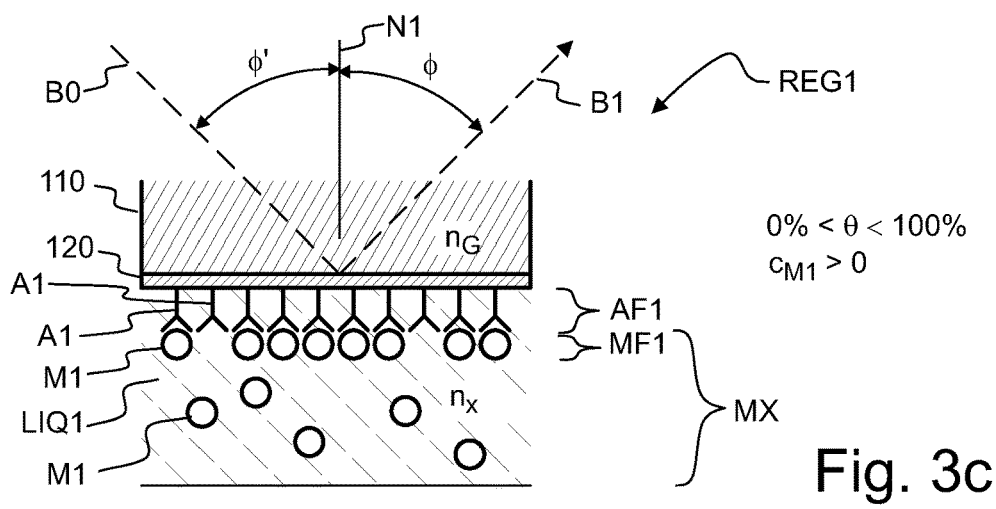
FIG. 3c shows, by way of example, the sample region when the surface coverage is greater than zero.

FIG. 3c shows a situation where the sample comprises adsorbate molecules M1 carried in a liquid LIQ1, and adsorbate molecules M1 may have been bound to the active sites A1 of the functional layer AF1. The concentration $c_{M1}$ of adsorbate molecules M1 in the bulk material LIQ1 may be greater than zero. The surface concentration $c_{M1,SRF}$ of molecules M1 on the functional layer AF1 may be substantially higher than in the situation of FIG. 3a or 3b. The adsorbate molecules M1 attached to the functional layer AF1 may form a molecular film MF1. The molecular film MF1 may at least partially cover the functional layer AF1. The surface coverage θ may be greater than zero but smaller than 100%.

Figure 3D:
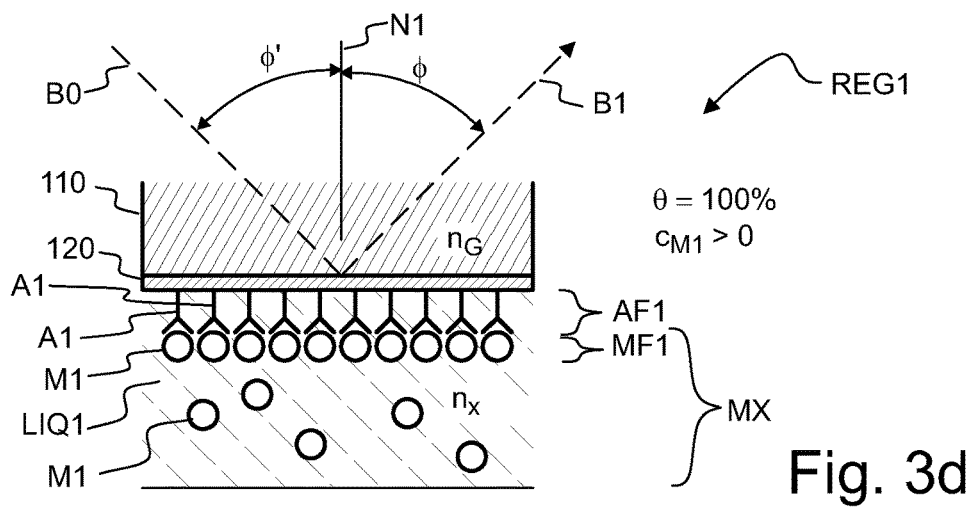
FIG. 3d shows, by way of example, in a cross sectional view, the sample region when the surface coverage is 100% and the bulk material contains adsorbate molecules.

FIG. 3d shows a situation where the sample MX comprises adsorbate molecules M1 carried in a bulk material LIQ1, and adsorbate molecules M1 have been bound to a high number of active sites A1 of the functional layer AF1. The surface concentration $c_{M1,SRF}$ of molecules M1 on the functional layer AF1 may be substantially higher than in the situation of FIG. 3a, 3b or 3c. In an embodiment, the surface coverage θ may be substantially equal to 100%. The concentration $c_{M1}$ of adsorbate molecules M1 in the bulk material LIQ1 may be greater than zero. The molecular film MF1 may substantially completely cover the functional layer AF1.

Figure 3E:
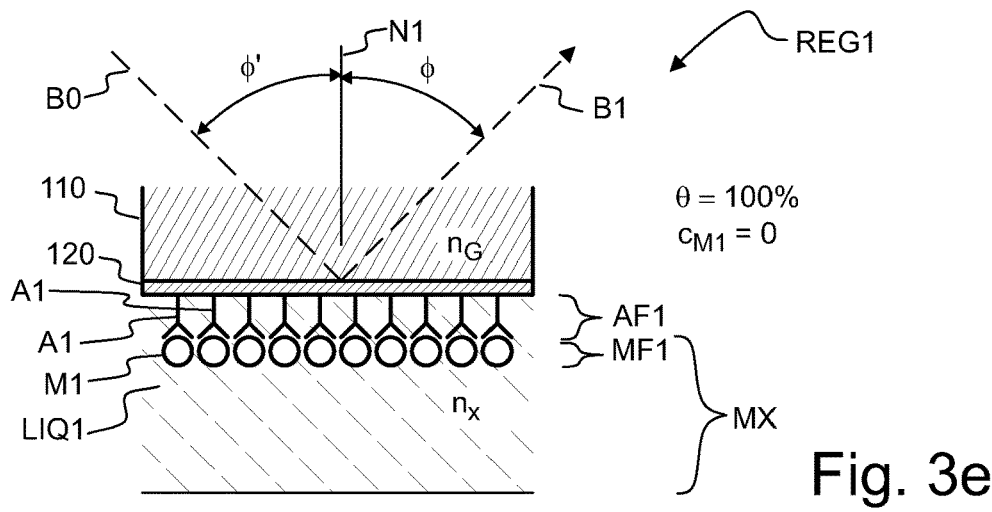
FIG. 3e shows, by way of example, in a cross sectional view, the sample region when the surface coverage is 100%.

FIG. 3e shows a situation where the sample MX does not comprise adsorbate molecules M1 carried in the bulk material LIQ1, but adsorbate molecules M1 have been bound to a high number of active sites A1 of the functional layer AF1. The surface concentration $c_{M1,SRF}$ of molecules M1 on the functional layer AF1 may be substantially higher than in the situation of FIG. 3a, 3b or 3c. In an embodiment, adsorbate molecules M1 may have been bound to substantially all active sites A1 of the functional layer AF1. The surface coverage θ may be substantially equal to 100%. The concentration $c_{M1}$ of adsorbate molecules M1 may be substantially equal to zero.

Figure 3F:
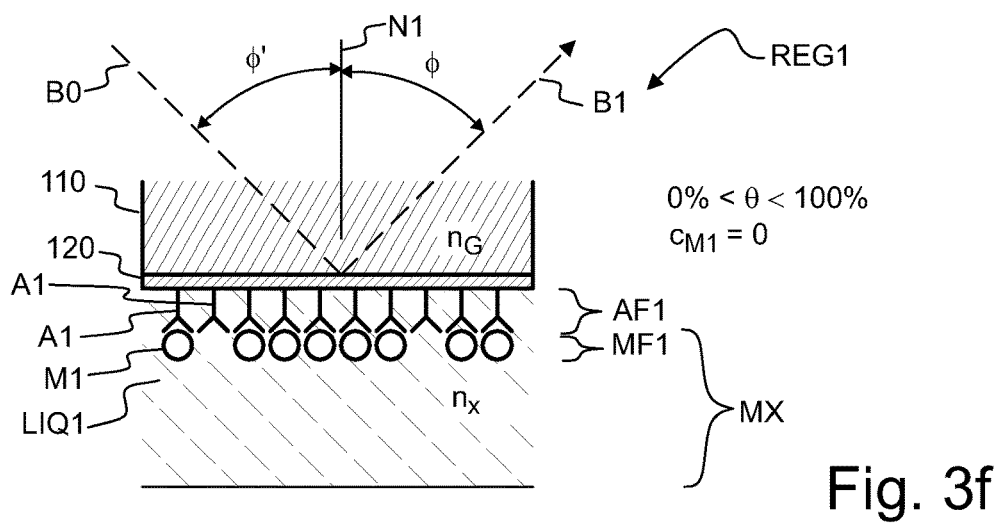
FIG. 3f shows, by way of example, in a cross sectional view, the sample region when the surface coverage is less than 100%.

FIG. 3f shows a situation where the sample MX does not comprise adsorbate molecules M1 carried in the bulk material LIQ1. Adsorbate molecules M1 are bound to some active sites A1 of the functional layer AF1. The surface concentration $c_{M1,SRF}$ of molecules M1 on the functional layer AF1 may be substantially lower than in case of FIG. 3e. The surface coverage θ may be greater than zero but smaller than 100%. The bulk concentration $c_{M1}$ of adsorbate molecules M1 may be substantially equal to zero.

Figure 4:
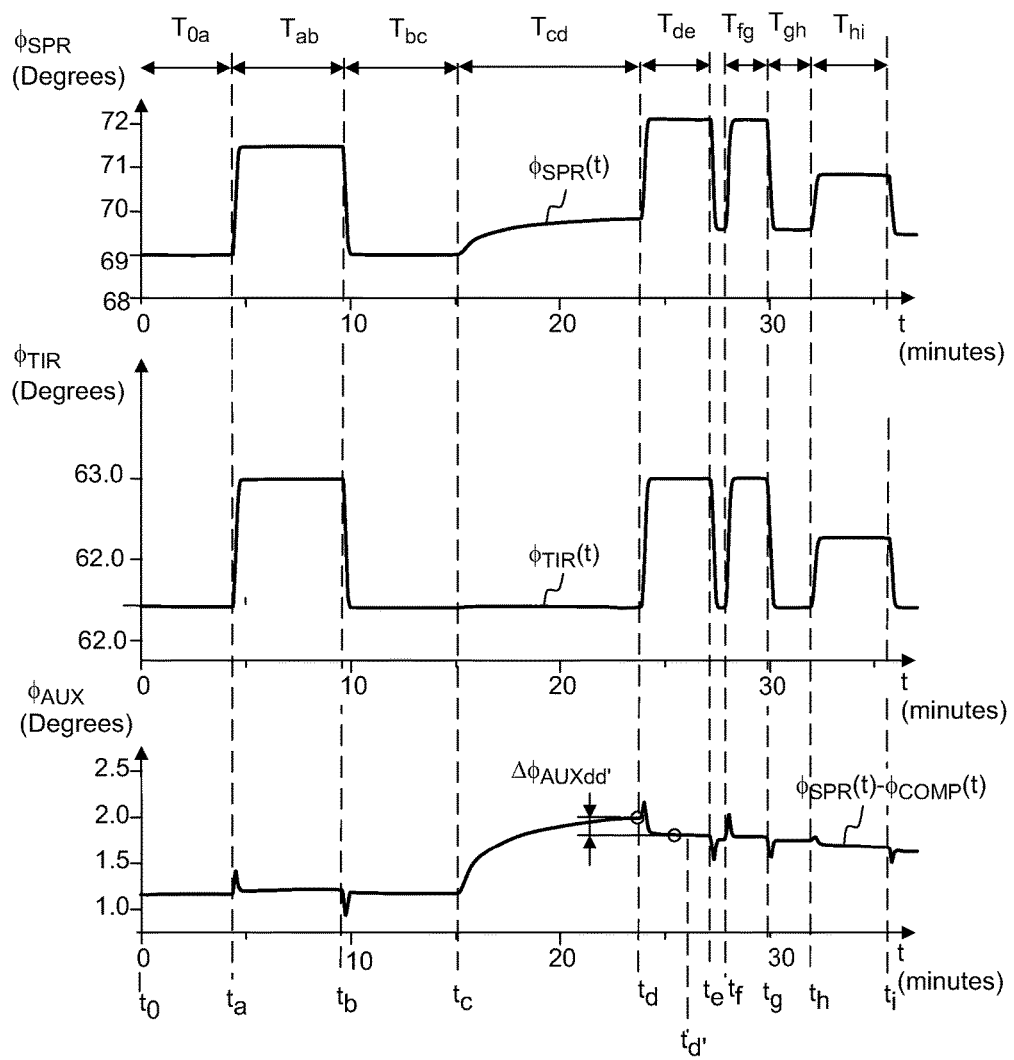
FIG. 4 shows, by way of example, temporal evolution of angle values during an adsorption/desorption test.

FIG. 4 shows angle values measured during a test, which involved binding of molecules M1 to a functional layer AF1. The uppermost curve of FIG. 4 shows temporal evolution of the surface plasmon resonance angle $\phi_{SPR}$. The second curve from the top in FIG. 4 shows temporal evolution of the critical angle $\phi_{TIR}$. The lowermost curve of FIG. 4 shows the auxiliary angle values $\phi_{AUX}(t)$ corresponding to the surface plasmon resonance angles $\phi_{SPR}(t)$ and the critical angles $\phi_{TIR}(t)$. The auxiliary angle values $\phi_{AUX}(t)$ may be calculated e.g. according to the equation (6d) by subtracting the compensating angle values $\phi_{COMP}(t)$ from the measured surface plasmon resonance angles $\phi_{SPR}(t)$. The compensating angle values $\phi_{COMP}(t)$ may be determined from the measured critical angles $\phi_{TIR}(t)$ by using the regression function $f_1(\phi_{TIR}(t))$. The compensating angle values $\phi_{COMP}(t)$ may be determined from the measured critical angles $\phi_{TIR}(t)$ e.g. by using a regression function $f_1(\phi_{TIR}(t))$ illustrated in FIG. 5.

In this example, the molecules M1 were protein molecules, and the functional layer AF1 comprised carboxymethyl dextran hydrogel (CMD-3D). During the time period $T_{ab}$, the functional layer AF1 was activated by exposing it to an activation solution, which comprised EDC and NHS. EDC means 1-Ethyl-3-(3-dimethylaminopropyl carbodiimide. NHS means N-hydroxysuccinimide. During the time period $T_{ab}$, the functional layer AF1 was exposed to a MES-buffer, which comprised protein molecules M1. MES means 2-(N-morpholino)ethanesulfonic acid. During the time periods $T_{de}$ and $T_{fg}$, the functional layer AF1 was deactivated by exposing it to a solution, which comprised ethanolamine. During the time period $T_{cd}$, non-specifically bound protein molecules were removed by exposing the layer AF1 to a solution, which comprised sodium hydroxide (NaOH).

The time period $T_{0a}$ starts at the time $t_0$ and ends at the time $t_a$. The time period $T_{ab}$ starts at the time $t_a$ and ends at the time $t_b$. The time period $T_{bc}$ starts at the time $t_b$ and ends at the time $t_c$. The time period $T_{cd}$ starts at the time $t_c$ and ends at the time $t_d$. The time period $T_{de}$ starts at the time $t_d$ and ends at the time $t_e$. The time period $T_{fg}$ starts at the time $t_f$ and ends at the time $t_g$. The time period $T_{gh}$ starts at the time $t_g$ and ends at the time $t_h$. The time period $T_{hi}$ starts at the time $t_0$ and ends at the time $t_i$.

During the time period $T_{0a}$, the functional layer AF1 was exposed to MES buffer, which did not contain EDC and NHS. During the time period $T_{ab}$, the functional layer AF1 was exposed to MES buffer, which contained EDC and NHS. During the time period $T_{bc}$, the functional layer AF1 was exposed to MES buffer, which did not contain EDC and NHS. The presence of EDC and NHS in the sample region REG1 during the time period $T_{ab}$ increased the surface plasmon resonance angle $\phi_{SPR}$. Reducing the concentrations of the EDC and NHS decreased the surface plasmon resonance angle $\phi_{SPR}$.

However, the auxiliary angle value $\phi_{AUX}$ may remain substantially constant during the time period from $t_0$ to $t_c$ even when the concentrations of EDC and NHS are varied. The substantially constant value of the auxiliary angle $\phi_{AUX}$ may be an indication that the activation by using EDC-NHS during the time period $T_{ab}$ did not substantially change the amount of molecules bound to the functional layer AF1.

During the time periods $T_{de}$ and $T_{fg}$, the functional layer AF1 was deactivated by exposing it to a solution, which comprised ethanolamine. $\phi_{AUX}(t_d)$ denotes the auxiliary angle value $\phi_{AUX}$ at the end of the time period $T_{cd}$. $t_{d'}$ denotes the midpoint of the time period $T_{de}$. $\phi_{AUX}(t_{d'})$ denotes the auxiliary angle value $\phi_{AUX}$ at the midpoint $t_{d'}$ of the time period $T_{de}$. $\Delta\phi_{AUXdd'}$ denotes the difference $\phi_{AUX}(t_{d'})-\phi_{AUX}(t_d)$. The auxiliary angle value $\phi_{AUX}(t_{d'})$ at the midpoint of the period $T_{de}$ may be lower than the auxiliary angle value $\phi_{AUX}(t_d)$ at the end $t_d$ of the preceding time period $T_{cd}$. The negative change $\Delta\phi_{AUXdd'}$ of the auxiliary angle may indicate that the amount of molecules M1 contained in the resonance volume RZ1 of the sample region REG1 was reduced after injection of the molecules M1 to the MES solution was stopped.

The measuring apparatus 500 may be arranged to operate such that the surface plasmon resonance angle $\phi_{SPR}$ and the critical angle $\phi_{TIR}(t)$ are not measured simultaneously. Consequently, the auxiliary angle values $\phi_{AUX}(t)$ calculated from the measured angles $\phi_{SPR}(t)$ and $\phi_{TIR}(t)$ may exhibit temporary disturbances in the vicinity of the transition times (e.g. in the vicinity of the times $t_0$ or $t_b$). The disturbances may be called e.g. as glitches. The temporary glitches may be caused by a time lag $\Delta t_{LAG}$ between measuring a critical angle value $\phi_{TIR}(t)$ and a surface plasmon resonance angle value $\phi_{SPR}(t+\Delta t_{LAG})$. In an embodiment, the time lag $\Delta t_{LAG}$ may be compensated e.g. by temporally shifting the measured values.

Figure 5:
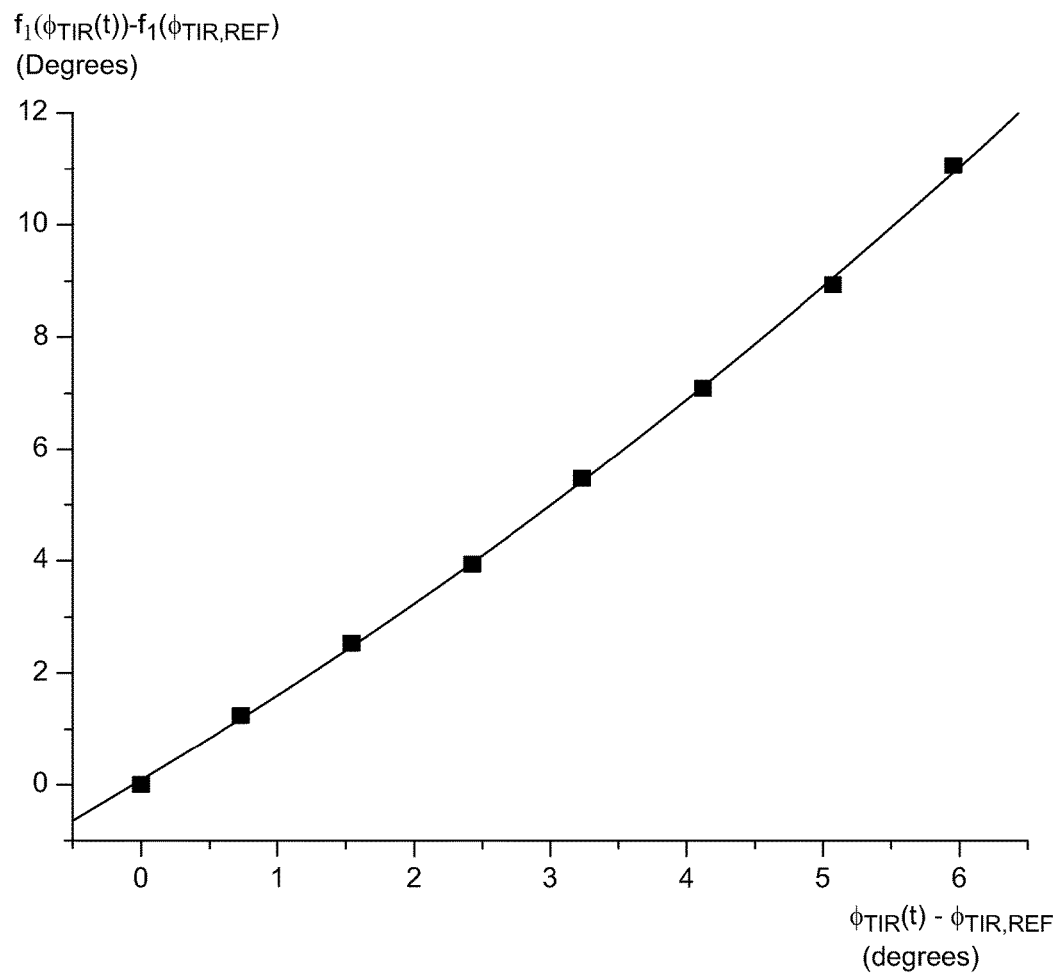
FIG. 5 shows, by way of example, determining a compensating angle value by using a regression function.

FIG. 5 shows, by way of example, how the regression function $f_1(\phi_{TIR}(t))$ may depend on the critical angle $\phi_{TIR}(t)$ The ordinate values show the difference $f_1(\phi_{TIR}(t))-$ $f_1(\phi_{TIR,REF})$ as a function of the difference $\phi_{TIR}(t)-\phi_{TIR,REF}$. $\phi_{TIR,REF}$ denotes a reference value of the critical angle. $f_1(\phi_{TIR,REF})$ denotes the value of the regression function $f_1(\phi_{TIR})$ when the critical angle $\phi_{TIR}$ is equal to the reference value $\phi_{TIR,REF}$.

The regression function $f_1(\phi_{TIR})$ may be a substantially linear function in a narrow angular range. In an embodiment, the regression function $f_1(\phi_{TIR})$ may be a linear function in an angular range, wherein the width of said angular range may be e.g. smaller than 6°.

Figure 6:
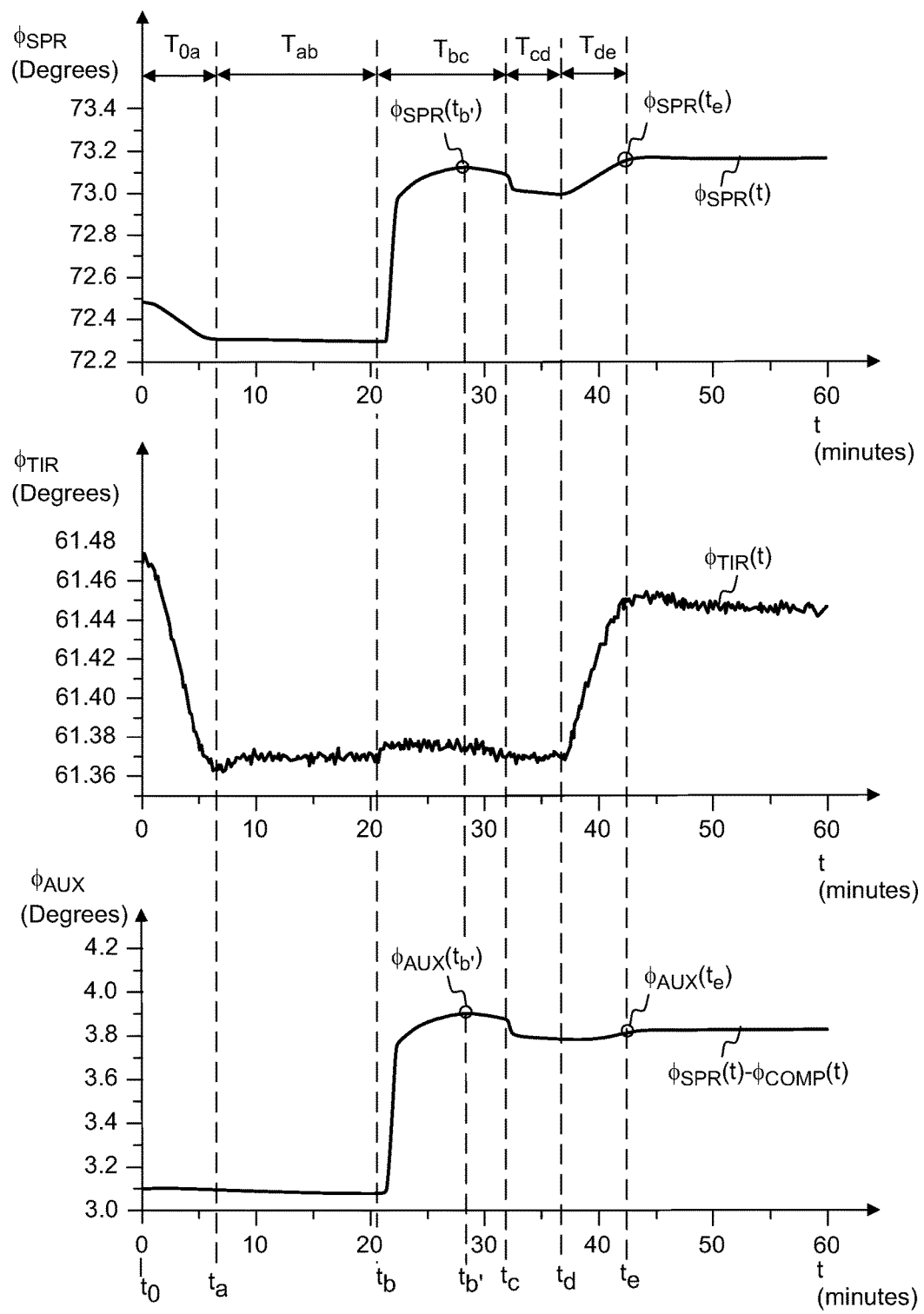
FIG. 6 shows, by way of example, temporal evolution of angle values during an adsorption test.

FIG. 6 show angle values $\phi$ measured during a test, which involved binding of structures M1 to a functional layer AF1. In this case, the structures M1 were dimyristoylphosphadithylcholine (DMPC) liposomes. The liposomes M1 may be prepared e.g. by a sonication. The functional layer AF1 was a lipid self-assembly implemented on a layer of silica ($SiO_2$).

During the time period $T_{0a}$, the temperature of the buffer solution was changed from 20° C. to 32° C. During the time period $T_{0a}$, the functional layer AF1 was exposed to an aqueous buffer solution, which comprised 10 mM 4-(2-hydroxyethyl)-1-piperazineethanesulfonic acid (HEPES), 140 mM sodium chloride (NaCl), and 3 mM $CaCl_2$.

During the time period $T_{bc}$, the functional layer AF1 was exposed to a mixture, which contained liposomes M1 in the aqueous buffer solution, which comprised 10 mM 4-(2-hydroxyethyl)-1-piperazineethanesulfonic acid (HEPES), 140 mM sodium chloride (NaCl), and 3 mM $CaCl_2$. The concentration of the liposomes M1 was 0.1 mg/mL. During the time period $T_{bc}$, the temperature of the buffer solution was 32° C. The injection of liposomes M1 to the buffer solution was stopped at the time $t_c$.

During the time period $T_{de}$, the temperature of the buffer solution was changed from 32° C. to 20° C.

The uppermost curve of FIG. 6 shows temporal evolution of the surface plasmon resonance angle $\phi_{SPR}$. The second curve from the top in FIG. 6 shows temporal evolution of the critical angle $\phi_{TIR}$. The lowermost curve of FIG. 6 shows the auxiliary angle value $\phi_{AUX}$. The auxiliary angle value $\phi_{AUX}(t)$ may be calculated e.g. according to equation (3) by subtracting the compensating angle value $\phi_{COMP}(t)$ from the measured surface plasmon resonance angle $\phi_{SPR}(t)$. The compensating angle values $\phi_{COMP}(t)$ may be determined from the measured critical angles $\phi_{TIR}(t)$ by using the regression function $f_1(\phi_{TIR})$. The compensating angle values $\phi_{COMP}$ may be determined from the measured critical angles $\phi_{TIR}(t)$ e.g. by using the regression function illustrated in FIG. 5.

The change of the temperature of the buffer solution during the cooling time period $T_{de}$ causes an increase of the critical angle $\phi_{TIR}$. The surface concentration $c_{M1,SRF}$ of the liposomes M1 on the functional layer AF1 is not expected to rise during the cooling time period $T_{de}$ because the injection of the liposomes M1 was already stopped before the start of the cooling time period $T_{de}$. The surface plasmon resonance angle $\phi_{SPR}(t)$ rises during the cooling time period $T_{de}$ although the surface concentration $c_{M1,SRF}$ of the liposomes M1 is not increased. The auxiliary angle value $\phi_{AUX}(t)$ may remain substantially constant during the cooling time period $T_{de}$. The auxiliary angle value $\phi_{AUX}(t)$ may attain a maximum value at the time $t_{b'}$. In particular, the auxiliary angle value $\phi_{AUX}(t_e)$ attained at the end to of the cooling time period $T_{de}$ may remain lower than the maximum auxiliary angle value $\phi_{AUX}(t_b)$ attained during the injection time period $T_{bc}$.

The auxiliary angle value $\phi_{AUX}(t)$ may be used as an indicator for the surface concentration $c_{M1,SRF}$ of the liposomes M1 on the functional layer AF1. The auxiliary angle value $\phi_{AUX}(t)$ may be less dependent on the temperature of the sample than the surface plasmon resonance angle $\phi_{SPR}(t)$. The auxiliary angle value $\phi_{AUX}(t)$ may be used as a selective indicator for the surface concentration $c_{M1,SRF}$ of the liposomes M1 on the functional layer AF1. The auxiliary angle value $\phi_{AUX}(t)$ may take into account the disturbing effect caused by a change of the refractive index of the buffer solution. The change of the refractive index may, in turn, be caused by the change of temperature.

Referring to FIG. 7a, the method may be used e.g. for monitoring binding of an analyte M1 to immobilized molecules M2. The method may be used for monitoring the surface concentration $c_{M1,SRF}$ of the analyte M1 at the sample region REG1. The analyte molecules M1 may be e.g. drug molecules. The immobilized molecules M2 may be e.g. organic molecules. The immobilized organic molecules M2 may be e.g. protein molecules, nucleotide molecules and/or hydrocarbon molecules. The immobilized molecules M2 may have been directly or indirectly attached to the metal layer 120 of the sample region REG1. The immobilized molecules M2 may have active sites A1. The active sites A1 of the immobilized molecules M2 may be substantially in a single plane. Alternatively, the active sites A1 of the immobilized molecules M2 may be in a substantially three-dimensional configuration (i.e. a different distances from the metal layer 120). For example, the immobilized molecules M2 may be attached to carboxymethyldextran (CMD-3D), which forms a three-dimensional (3D) matrix.

The analyte M1 may be initially carried in the bulk material LIQ1, which may comprise a substance M0. The substance M0 may be e.g. water. The bulk material LIQ1 may mainly consist of the substance M0. The bulk material LIQ1 may be e.g. an aqueous solution. The concentration $c_{M0}$ of water in the aqueous solution may be e.g. greater than 50%, greater than 90%, greater than 95%, or even greater than 99%.

The bulk material LIQ1 may further comprise an additive M3. The aqueous solution LIQ1 may comprise varying amounts of an additive M3. The additive M3 may be e.g. a solubility-enhancing additive and/or a stabilizing additive. A solubility-enhancing additive M3 may increase the solubility of the analyte M1 in the bulk material LIQ1. A stabilizing additive M3 may increase the stability of the analyte M1 in the bulk material LIQ1. The stabilizing additive M3 may e.g. reduce or prevent protein denaturation. The solubility-enhancing and/or stabilizing additive M3 may be water-soluble. For example, the additive M3 may be dimethyl sulfoxide (DMSO), methylsulfonylmethane (MSM, $DMSO_2$), acetonitrile, or ethylene glycol.

The method may comprise varying the concentration $c_{M1}$ of the analyte M1, and/or varying the concentration $c_{M3}$ of the additive M3 in the bulk material LIQ1, which is guided to the sample volume ZV1. The method may be used for monitoring surface concentration $c_{M1,SRF}$ of the analyte M1 at the sample region REG1. The method may be used for monitoring a change of surface concentration $c_{M1,SRF}$ of the analyte M1 at the sample region REG1.

The method may comprise:
measuring a first surface plasmon resonance angle value $\phi_{SPR,REF}$ of a sample region REG1,
measuring a first critical angle value $\phi_{TIR,REF}$ of the sample region REG1,
causing a change of surface concentration $c_{M1,SRF}$ of an analyte M1 at the sample region REG1,
changing the bulk composition at the sample region REG1, measuring a second surface plasmon resonance angle value $\phi_{SPR}(t)$ of the sample region REG1, measuring a second critical angle value $\phi_{TIR}(t)$ of the sample region (REG1), and determining an indicator value $\phi_{AUX}(t)$ indicative of the change of the surface concentration $c_{M1,SRF}$, wherein the indicator value $\phi_{AUX}(t)$ is determined from the second surface plasmon resonance angle value $\phi_{SPR}(t)$ by compensating an effect of the bulk composition, and wherein the magnitude $\phi_{COMP}$ of said effect is determined by using the second critical angle value $\phi_{TIR}(t)$.

The bulk composition $c_{M1}$, $c_{M2}$, $c_{M3}$ of a sample MX and/or liquid LIQ1 may be indicated e.g. by specifying bulk concentrations of individual substances M0, M1, M2, M3 of the sample MX or liquid LIQ1.

The bulk composition at the sample region REG1 may be changed e.g. by changing the bulk concentration $c_{M3}$ in a liquid LIQ1, which is introduced to the sample region REG1. The bulk composition at the sample region REG1 may be changed e.g. by changing the bulk concentration $c_{M3}$ in a liquid LIQ1, which is introduced to a sample cell 100.

The bulk concentration may mean the amount of a substance per unit volume. For example, a unit volume $V_0$ may contain an amount $N_{M1,0}$ of a substance M1, and the bulk concentration $c_{M1}$ of said substance M1 may be equal to the amount $N_{M1,0}$ divided by said unit volume $V_0$. Thus, $c_{M1} = N_{M1,0}/V_0$. The amount of the substance M1 may mean the quantity of the substance M1, and the amount $N_{M1,0}$ may be expressed e.g. in moles. The bulk concentration $c_{M1}$ may be expressed e.g. by indicating the number of moles contained in the unit volume $V_0$. However, the bulk concentration $c_{M1}$ of the substance M1 may also be specified by indicating a volume fraction $V_{M1,0}/V_0$ or a mass fraction $m_{M1,0}/m_0$. The volume $V_{M1,0}$ may denote a volume occupied by the amount $N_{M1,0}$ of the substance M1 in a situation where the volume $V_{M1,0}$ would contain only the substance M1 at a reference temperature and at a reference pressure. The mass $m_{M1,0}$ may denote the mass of the amount $N_{M1,0}$ of the substance M1. $m_0$ may denote the mass of the unit volume $V_0$ of the sample MX.

The surface concentration $c_{M1,SRF}$ of the substance M1 may mean the excess amount of the substance M1 per unit area of the surface of the layer 120 over what would be present if the bulk concentration $c_{M1}$ of the substance M1 prevailed all the way to the surface 121 of the layer 120.

Referring back to FIG. 1b, the sample region REG1 may have the resonance volume RZ1 and the sample volume ZV1. $V_{RZ1}$ may denote the volume of the resonance volume RZ1, and $V_{ZV1}$ may denote the volume of the sample volume ZV1. $V_{RZ1}/V_{ZV1}$ denotes the ratio of the volume $V_{RZ1}$ of the resonance volume RZ1 to the volume $V_{ZV1}$ of the sample volume ZV1. The ratio $V_{RZ1}/V_{ZV1}$ may be substantially smaller than one. FIG. 2b shows the projection AR1 of the sample volume ZV1 on the layer 120. The projection AR1 may have a surface area $A_{ZV1}$.

The sample volume ZV1 may contain an amount $N_{M1,ZV1}$ of the substance M. The bulk concentration $c_{M1}$ of the substance M1 in the sample volume ZV1 may be substantially equal to the ratio $N_{M1,ZV1}/V_{ZV1}$. The resonance volume RZ1 may contain an amount $N_{M1,SRF}$ of the substance M1.

The surface concentration $c_{M1,SRF}$ of the substance M1 may mean the excess amount $(N_{M1,SRF} - N_{M1,EXT})$ divided by the surface area $A_{ZV1}$ of the projection AR1 of the sample volume ZV1, wherein said excess amount may be equal to the difference $(N_{M1,SRF} - N_{M1,EXT})$ between the amount $N_{M1,SRF}$ of the substance M1 contained in the resonance volume RZ1 and an extrapolated amount $N_{M1,EXT}$ of the substance M1, wherein the extrapolated amount $N_{M1,EXT}$ may be substantially equal to the bulk concentration $c_{M1}$ of the substance M1 multiplied by the volume $V_{RZ1}$ of the resonance volume RZ1. In other words, the extrapolated amount $N_{M1,EXT}$ may be equal to $N_{M1,ZV1} \cdot V_{RZ1}/V_{ZV1}$.

In an embodiment, the bulk concentration $c_{M1}$ of the substance M1 in the sample volume ZV1 may substantially deviate from the initial bulk concentration of said substance M1 in the liquid LIQ1, which is introduced into the sample cell 100. The difference may be caused e.g. by adsorption to the surfaces and/or by limited rate of diffusion in the vicinity of the layer 120.

Figure 7E:
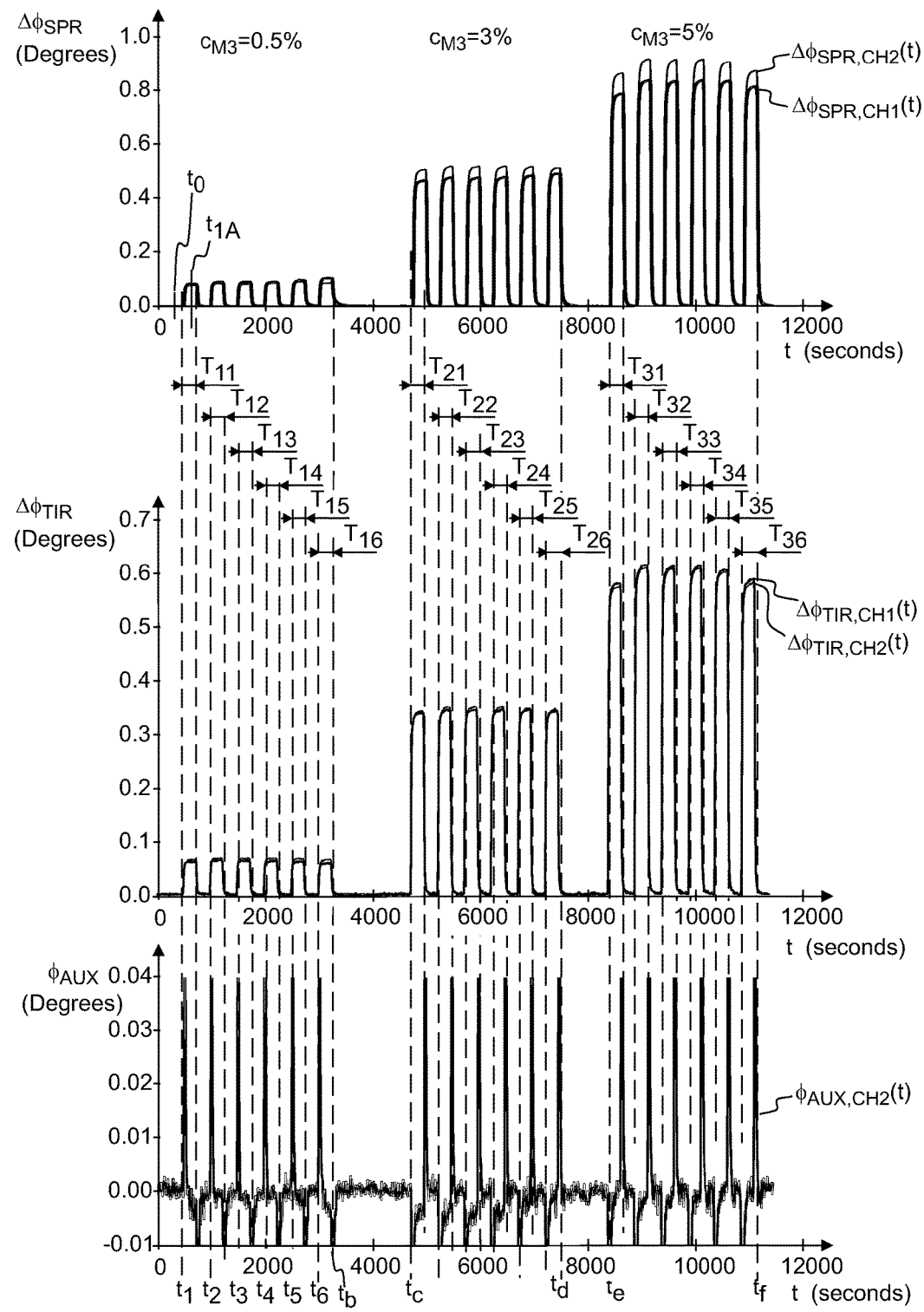
FIG. 7e shows, by way of example, temporal evolution of angle values during a second reference adsorption test associated with the first adsorption test of FIG. 7c.

FIGS. 7c to 7e illustrate, by way of example, monitoring surface concentration $c_{M1,SRF}$ of an analyte M1 during tests where the bulk concentration $c_{M1}$ of the analyte M1, and/or the bulk concentration $c_{M3}$ of the additive M3 were varied. In this example, the analyte was a drug, the immobilized molecules M2 were albumin molecules, and the additive M3 was dimethyl sulfoxide (DMSO). However, the method may be used for monitoring surface concentration $c_{M1,SRF}$ of the analyte M1 also in case of other analytes M1, other immobilized molecules M2, and/or other additives M3.

The sample region REG1 may comprise immobilized organic molecules M2 capable of binding to the molecules of the analyte M1. The immobilized organic molecules M2 may be e.g. protein molecules, nucleotide molecules and/or carbohydrate molecules. The method may comprise varying the bulk concentration $c_{M3}$ of an additive M3, which may be e.g. a stabilizing additive and/or a solubility-enhancing additive.

FIG. 7c shows temporal evolution of angle values measured during a first test, which involved binding of a drug to human serum albumin (HSA). The first test was made by using a first sample region, wherein the functional layer of the first sample region comprised immobilized human serum albumin (HSA).

FIG. 7d shows temporal evolution of bulk concentrations and angle values during a first part of the first test.

FIG. 7e shows temporal evolution of angle values measured during a second test. The second test was made by using a second sample region REG2, wherein the functional layer of the second sample region REG2 did not comprise human serum albumin (HSA). The second test may also be called e.g. as the reference test.

FIG. 7b shows the first sample region REG1 and the second sample region REG2. The functional layer AF1 of the second sample region REG2 was otherwise similar to the functional layer AF1 of the first sample region REG1, except that the functional layer AF1 of the first sample region REG1 comprised HSA. The functional layer AF1 of the second sample region REG2 was formed such that the functional layer AF1 of the second sample region REG2 did not contain HSA. B0b denotes the input beam impinging on the second sample region REG2, and B1b denotes the reflected beam reflected from the second sample region REG2. ZV2 denotes the sample volume of the second sample region REG2.

The first test and the second test were made substantially simultaneously by using substantially similar sample compositions. Measurements may be made by using the first sample region REG1 and the second sample region REG1 substantially simultaneously. However, the second test may also be made before or after the first test. For example, the functional layer AF1 of the first sample region REG1 may be removed from the conductive layer 120 after the first test, and a new functional layer may be formed on the same conductive layer 120 so as to form the second sample region REG2 for the second test.

Prior to the first test, the functional layer AF1 of the first sample region was formed by a method, which comprised:
  attaching a layer of CMD-3D to the metal layer 120 of the sensor,
  washing the layer of CMD-3D with an aqueous solution, which comprised 2M NaCl (sodium chloride) and 10 mM NaOH (sodium hydroxide),
  activating the layer of CMD-3D with an activation solution, which comprised EDC and NHS.
  immobilizing HSA to the layer of CMD-3D, by treating the layer of CMD-3D with an aqueous solution, which comprised MES and HSA (the bulk concentration of MES was 5 mM and pH 5.0),
  deactivating the functional layer AF1 by exposing it to an aqueous solution, which comprised ethanolamine (pH 8.0).
  removing non-specifically bound HSA by washing the functional layer AF1 with an aqueous solution, which comprised 50 mM NaOH.

The immobilization of human serum albumin was performed in-situ according to the EDC-NHS chemistry as described in the article by Rich R. et al., Anal Biochem. 296 (2001), pages 197-207.

Prior to the second test, the functional layer AF1 of the second sample region was formed by a method, which comprised:
  attaching a layer of CMD-3D to the metal layer 120 of the sensor,
  washing the layer of CMD-3D with an aqueous solution, which comprised 2M NaCl and 10 mM NaOH,
  activating the layer of CMD-3D with an activation solution, which comprised EDC and NHS.
  treating the layer of CMD-3D with an aqueous solution, which comprised MES (the bulk concentration of MES was 5 mM and pH 5.0),
  deactivating the functional layer AF1 by exposing it to an aqueous solution, which comprised ethanolamine (pH 8.0).
  washing the functional layer AF1 with an aqueous solution, which comprised 50 mM NaOH.

CMD-3D means carboxymethyldextran, which forms a three-dimensional matrix. NaCl means sodium chloride. NaOH means sodium hydroxide. EDC means N-ethyl-N'-(3-(dimethylamino)propyl)carbodiimide. NHS means N-hydroxysuccinimide. MES means 2-(N-morpholino)ethanesulfonic acid. HSA means human serum albumin.

The tests involved varying the concentrations $c_{M1}$ of a drug carried in a PBS buffer, and varying the concentrations $c_{M3}$ of DMSO. DMSO means Dimethyl sulfoxide. During the first test and the second test, the functional layers were exposed to an aqueous solution, which comprised phosphate buffered saline (PBS), and varying concentrations of a drug and DMSO. In this example, the drug was indomethacine. However, also other drugs may be studied by using a similar method. The binding of a drug to a functional surface may be studied by using a similar method.

The bulk concentrations $c_{M1}$ of the drug and the bulk concentrations $c_{M3}$ of the additive M3 (DMSO) were varied during the first test and the second test. The tests comprised time periods $T_{11}$, $T_{12}$, $T_{13}$, $T_{14}$, $T_{15}$, $T_{16}$, $T_{21}$, $T_{22}$, $T_{23}$, $T_{24}$, $T_{25}$, $T_{26}$, $T_{31}$, $T_{32}$, $T_{33}$, $T_{34}$, $T_{35}$, $T_{36}$. Table 1 shows the bulk concentrations $c_{M1}$ of the drug and the bulk concentrations $c_{M3}$ of DMSO during said time periods $T_{11}$, $T_{12}$, $T_{13}$, $T_{14}$, $T_{15}$, $T_{16}$, $T_{21}$, $T_{22}$, $T_{23}$, $T_{24}$, $T_{25}$, $T_{26}$, $T_{31}$, $T_{32}$, $T_{33}$, $T_{34}$, $T_{35}$, $T_{36}$.

TABLE 1

The concentrations $c_{M1}$ of the drug and the bulk concentrations $c_{M3}$ of the additive M3 used in the first and the second test.

| | | |
|---|---|---|
| $T_{11}$ | $c_{M3}$ = 0.5% | $c_{M1}$ = 0.00 μM |
| $T_{12}$ | $c_{M3}$ = 0.5% | $c_{M1}$ = 0.01 μM |
| $T_{13}$ | $c_{M3}$ = 0.5% | $c_{M1}$ = 0.1 μM |
| $T_{14}$ | $c_{M3}$ = 0.5% | $c_{M1}$ = 1 μM |
| $T_{15}$ | $c_{M3}$ = 0.5% | $c_{M1}$ = 10 μM |
| $T_{16}$ | $c_{M3}$ = 0.5% | $c_{M1}$ = 50 μM |
| $T_{21}$ | $c_{M3}$ = 3% | $c_{M1}$ = 0.00 μM |
| $T_{22}$ | $c_{M3}$ = 3% | $c_{M1}$ = 0.01 μM |
| $T_{23}$ | $c_{M3}$ = 3% | $c_{M1}$ = 0.1 μM |
| $T_{24}$ | $c_{M3}$ = 3% | $c_{M1}$ = 1 μM |
| $T_{25}$ | $c_{M3}$ = 3% | $c_{M1}$ = 10 μM |
| $T_{26}$ | $c_{M3}$ = 3% | $c_{M1}$ = 50 μM |
| $T_{31}$ | $c_{M3}$ = 5% | $c_{M1}$ = 0.00 μM |
| $T_{32}$ | $c_{M3}$ = 5% | $c_{M1}$ = 0.01 μM |
| $T_{33}$ | $c_{M3}$ = 5% | $c_{M1}$ = 0.1 μM |
| $T_{34}$ | $c_{M3}$ = 5% | $c_{M1}$ = 1 μM |
| $T_{35}$ | $c_{M3}$ = 5% | $c_{M1}$ = 10 μM |
| $T_{36}$ | $c_{M3}$ = 5% | $c_{M1}$ = 50 μM |

The unit M denotes herein one mole per liter. For example $c_{M1}$=0.1 μM means that the (initial) bulk concentration $c_{M1}$ is 0.1 moles per liter. The bulk concentrations $c_{M3}$ of Table 1 are expressed as relative volume fractions of the additive M3. The concentrations $c_{M1}$ and $c_{M3}$ of Table 1 indicate the initial bulk concentrations in the liquid LIQ1 when it was introduced into the sample cell 100.

The bulk concentrations $c_{M1}$ of the drug and the bulk concentrations $c_{M3}$ of the additive M3 (DMSO) in the sample volume ZV1 of the first sample region REG1 may substantially correspond to the values shown in Table 1.

The bulk concentrations $c_{M1}$ of the drug and the bulk concentrations $c_{M3}$ of the additive M3 (DMSO) in the sample volume of the second sample region may substantially correspond to the values shown in Table 1.

The bulk concentrations $c_{M1}$ in the sample volume of the second sample region may be substantially equal to the bulk concentrations $c_{M1}$ in the sample volume of the first sample region, and the bulk concentrations $c_{M3}$ in the sample volume of the second sample region may be substantially equal to the bulk concentration $c_{M1}$ of the drug in the sample volume of the first sample region.

The bulk concentration $c_{M1}$ of the drug and the bulk concentration $c_{M3}$ of DMSO were substantially equal to zero immediately before each time period $T_{11}$, $T_{12}$, $T_{13}$, $T_{14}$, $T_{15}$, $T_{16}$, $T_{21}$, $T_{22}$, $T_{23}$, $T_{24}$, $T_{25}$, $T_{26}$, $T_{31}$, $T_{32}$, $T_{33}$, $T_{34}$, $T_{35}$, $T_{36}$. In particular, the bulk concentration $c_{M1}$ and the bulk concentration $c_{M3}$ of DMSO were equal to zero between the time periods $T_1$ and $T_2$.

The time period $T_{11}$ started at the time $t_1$. The time period $T_{12}$ started at the time $t_2$. The time period $T_{13}$ started at the time $t_3$. The time period $T_{14}$ started at the time $t_4$. The time period $T_{15}$ started at the time $t_5$. The time period $T_{16}$ started at the time $t_6$, and the end of the time period $T_6$ was at the time $t_b$. The time period $T_{21}$ started at the time $t_b$. The time period $T_{26}$ ended at the time $t_d$. The time period $T_{31}$ started at the time $t_e$. The time period $T_{36}$ ended at the time $t_f$.

The uppermost curve of FIG. 7d shows temporal evolution of bulk concentration $c_{M1}(t)$ of the drug during a first part of the first test (and also during the first part of the second test). The first part of the first test comprised the time periods $T_{11}$, $T_{12}$, $T_{13}$, $T_{14}$, $T_{15}$, $T_{16}$. The bulk concentration $c_{M1}$ was varied between the zero concentration and the values 0.01 µM, 0.1 µM, 1 µM, 10 µM and 50 µM as shown in FIG. 7d and as indicated in Table 1. The bulk concentration $c_{M1}$ was substantially equal to zero during the time period $T_{11}$.

The second curve from the top in FIG. 7d shows temporal evolution of bulk concentration $c_{M3}(t)$ of the additive M3 (DMSO) during a first part of the first test (and also during the first part of the second test).

$t_0$ denotes a reference time. The reference time $t_0$ may be selected such that the bulk concentrations $c_{M1}$ and $c_{M3}$ are substantially equal to zero at the time $t_0$. The time $t_0$ may be e.g. before the time $t_1$ or between the time periods $T_{11}$ and $T_{12}$. $t_{1A}$ denotes a time which is between the start and the end of the time period $T_{11}$. $t_{1B}$ denotes a time, which is between the time periods $T_{11}$ and $T_{12}$.

The third curve from the top in FIG. 7d shows temporal evolution of surface plasmon resonance angle $\phi_{SPR,CH1}(t)$ of the first sample region during the first part of the first test. The surface plasmon resonance angle $\phi_{SPR,CH1}(t)$ may have a first value $\phi_{SPR1}$ at the time $t_0$, and a second value $\phi_{SPR2}$ at the time $t_{1A}$. $\Delta\phi_{SPR12}$ denotes the difference $\phi_{SPR2}-\phi_{SPR1}$.

The lowermost curve of FIG. 7d shows temporal evolution of critical angle $T_{TIR,CH1}(t)$ of the first sample region during the first part of the first test. The critical angle $\phi_{TIR,CH1}(t)$ may have a first value $\phi_{TIR1}$ at the time $t_0$, and a second value $\phi_{TIR2}$ at the time $t_{1A}$. $\Delta\phi_{TIR12}$ denotes the difference $\phi_{TIR2}-\phi_{TIR1}$.

The auxiliary angle value $\phi_{AUX,CH1}(t)$ may be calculated by subtracting the compensating angle value $\phi_{COMP}(t)$ from the measured resonance angle $\phi_{SPR,CH1}(t)$:

$$\phi_{AUX,CH1}(t)=\phi_{SPR,CH1}(t)-\phi_{COMP} \quad (7a)$$

The compensating angle value $\phi_{COMP}(t)$ may be calculated from the critical angle $\phi_{TIR,CH1}(t)$ by using a regression function $f_1$:

$$\phi_{COMP}(t)=f_1(\phi_{TIR,CH1}(t)) \quad (7b)$$

The regression function $f_1$ may be e.g. a linear function:

$$f_1(\phi_{TIR,CH1}=(t))=C\cdot(\phi_{TIR,CH1}(t)) \quad (7c)$$

The parameter C of the linear regression function $f_1$ may be determined e.g. by calculating the ratio $\Delta\phi_{SPR12}/\Delta\phi_{TIR12}$.

$$C = \frac{\phi_{SPR,CH1}(t_{1A}) - \phi_{SPR,CH1}(t_0)}{\phi_{TIR,CH1}(t_{1A}) - \phi_{TIR,CH1}(t_0)} \quad (7d)$$

The compensating angle value $\phi_{COMP}$ may be subsequently calculated from the critical angle $\phi_{TIR,CH1}(t)$ by using the parameter C:

$$\phi_{COMP}(t)=C\cdot\phi_{TIR,CH1}(t)+D \quad (7e)$$

The parameter C of the regression function $f_1((\phi_{TIR})$ may be determined by a method which comprises:
measuring a first auxiliary surface plasmon resonance angle $\phi_{SPR1}$ when the sample volume contains a first auxiliary sample,
measuring a first auxiliary critical angle $\phi_{TIR1}$ when the sample volume contains the first auxiliary sample,
measuring a second auxiliary surface plasmon resonance angle $\phi_{SPR2}$ when the sample volume contains a second auxiliary sample,
measuring a second auxiliary critical angle $\phi_{TIR2}$ when the sample volume contains the second auxiliary sample,
determining a change $\Delta\phi_{SPR12}$ of resonance angle by subtracting the first auxiliary resonance angle value $\phi_{SPR1}$ from the second auxiliary resonance angle value $\phi_{SPR2}$,
determining a change $\phi_{TIR12}$ of critical angle by subtracting the first auxiliary critical angle value $\phi_{TIR1}$ from the second auxiliary critical angle value $\phi_{TIR2}$, and
calculating the ratio of the change $\Delta\phi_{SPR12}$ of resonance angle to the change $\Delta\phi_{TIR12}$ of critical angle.

In an embodiment, the parameter D may be equal to zero.

$$\phi_{COMP}(t)=C\cdot(\phi_{TIR,CH1}(t)) \quad (7f)$$

Thus, the auxiliary angle value $\phi_{AUX,CH1}(t)$ for the first sample region may subsequently be calculated e.g. as follows:

$$\phi_{AUX,CH1}(t)=\phi_{SPR,CH1}(t)-C\cdot(\phi_{TIR,CH1}(t)) \quad (7g)$$

In an embodiment, the parameter D of the regression function may also have a value, which is different from zero. Thus, the auxiliary angle value $\phi_{AUX,CH1}(t)$ for the first sample region may subsequently be calculated e.g. as follows:

$$\phi_{AUX,CH1}(t)=\phi_{SPR,CH1}(t)-C\cdot(\phi_{TIR,CH1}(t))-D \quad (7h)$$

In particular, the parameter D may be selected such that the auxiliary angle value $\phi_{AUX,CH1}(t)$ at the time $t_0$ is equal to zero.

$$D=\phi_{SPR,CH1}(t_0)-C\cdot(\phi_{TIR,CH1}(t_0)) \quad (7i)$$

The uppermost curve of FIG. 7c shows temporal evolution of the angular difference $\Delta\phi_{SPR,CH1}(t)$ of the first sample region. The angular difference $\Delta\phi_{SPR,CH1}(t)$ may be determined e.g. by subtracting a reference value from the measured resonance angle $\phi_{SPR,CH1}(t)$. In particular, the angular difference $\Delta\phi_{SPR,CH1}(t)$ may be determined by calculating the difference $\phi_{SPR,CH1}(t)-\phi_{SPR,CH1}(t_0)$.

The second curve from the top in FIG. 7c shows temporal evolution of the angular difference $\Delta\phi_{TIR,CH1}(t)$ of the first sample region. The angular difference $\Delta\phi_{TIR,CH1}(t)$ may be determined e.g. by subtracting a reference value from the measured resonance angle $\phi_{TIR,CH1}(t)$. In particular, the angular difference $\Delta\phi_{TIR,CH1}(t)$ may be determined by calculating the difference $\phi_{TIR,CH1}(t)-\phi_{TIR,CH1}(t_0)$.

The lowermost curve of FIG. 7c shows temporal evolution of the auxiliary angle $\phi_{AUX,CH1}(t)$ of the first sample region. The curve $\phi_{AUX,CH1}(t)$ may be calculated e.g. by using the equation (7h), where the parameter C may be determined by using the equation (7d), and the parameter D may be determined by using the equation (7i).

In an embodiment, the curve $\phi_{AUX,CH1}(t)$ may also be calculated e.g. by using the equation (7g), where the parameter C may be determined by using the equation (7d).

The auxiliary angle $\phi_{AUX,CH1}(t)$ may have an average value $\phi_{AUX,4}$ during the time period $T_{14}$. The auxiliary angle $\phi_{AUX,CH1}(t)$ may have an average value $\phi_{AUX,5}$ during the time period $T_{15}$. The auxiliary angle $\phi_{AUX,CH1}(t)$ may have an average value $\phi_{AUX,6}$ during the time period $T_{16}$.

The auxiliary angle $\phi_{AUX,CH1}(t)$ may be indicative of molecular binding of the drug to the human serum albumin (HSA). The drug may be bound to the human serum albumin of the functional layer of the first sample region. An increase of the auxiliary angle $\phi_{AUX,CH1}(t)$ may indicate an increase of the occupied sites of the functional layer of the first sample region. The auxiliary angle $\phi_{AUX,CH1}(t)$ may be averaged over each time period $T_{11}$, $T_{12}$, $T_{13}$, $T_{14}$, $T_{15}$, $T_{16}$, $T_{21}$, $T_{22}$, $T_{23}$, $T_{24}$, $T_{25}$, $T_{26}$, $T_{31}$, $T_{32}$, $T_{33}$, $T_{34}$, $T_{35}$, $T_{36}$. An increase of the average value of the auxiliary angle $\phi_{AUX,CH1}(t)$ may indicate an increased number of the occupied sites of the functional layer of the first sample region. An increase of the average value of the auxiliary angle $\phi_{AUX,CH1}(t)$ may indicate an increased surface concentration $c_{M1,SRF}$ of the analyte molecules M1 (e.g. the drug). In this example, it may be noticed that the average value of the auxiliary angle $\phi_{AUX,CH1}(t)$ increases with increasing bulk concentration $c_{M1}$ of the drug in the bulk material. The auxiliary angle $\phi_{AUX,CH1}(t)$ may indicate that the number of occupied sites increased with increasing bulk concentration $c_{M1}$ of the drug.

FIG. 7e shows temporal evolution of the angular difference $\Delta\phi_{SPR,CH2}(t)$ of the second sample region. The angular difference $\Delta\phi_{SPR,CH2}(t)$ may be determined e.g. by subtracting a reference value from the measured resonance angle $\phi_{SPR,CH2}(t)$. In particular, the angular difference $\Delta\phi_{SPR,CH2}(t)$ may be determined by calculating the difference $\phi_{SPR,CH2}(t)-\phi_{SPR,CH2}(t_0)$.

The angular difference $\Delta\phi_{TIR,CH2}(t)$ may be determined e.g. by subtracting a reference value from the measured resonance angle $\phi_{SPR,CH2}(t)$. In particular, the angular difference $\Delta\phi_{TIR,CH2}(t)$ may be determined by calculating the difference $\phi_{TIR,CH2}(t)-\phi_{SPR,CH2}(t_0)$.

Equations (7a) to (7i) may be modified by replacing $\phi_{SPR,CH1}(t)$ with $\phi_{SPR,CH2}(t)$, and by replacing $\phi_{TIR,CH1}(t)$ with $\phi_{TIR,CH2}(t)$. The modified equations (7a) to (7i) may be used for calculating the auxiliary angle $\phi_{AUX,CH2}(t)$ of the second sample region.

The lowermost curve of FIG. 7e shows temporal evolution of the auxiliary angle $\phi_{AUX,CH2}(t)$ of the second sample region. The curve $\phi_{AUX,CH2}(t)$ may be calculated e.g. by using a modified equation (7h), where the parameter C may be determined by using a modified equation (7d), and the parameter D may be determined by using a modified equation (7i). The modified equations (7h), (7d), (7i) may be formed from the equations (7h), (7d), (7i) by replacing the markings CH1 with the markings CH2.

The parameter C of the regression function may have a first value $C_1$ for calculating the auxiliary angle $\phi_{AUX,CH1}(t)$ of the first sample region. The parameter C of the regression function may have a second value $C_2$ for calculating the auxiliary angle $\phi_{AUX,CH2}(t)$ of the second sample region. The value of the parameter C of the regression function may be specifically determined for each channel. In an embodiment, the second value $C_2$ may be different from the first value $C_1$.

It may be noticed that average value of the auxiliary angle $\phi_{AUX,CH2}(t)$ of the second sample region may be substantially independent of the bulk concentration $c_{M1}$ of the drug. The average value of the auxiliary angle $\phi_{AUX,CH2}(t)$ may remain substantially constant with increasing bulk concentrations $c_{M1}$. This may be an indication that the number of occupied sites of the functional layer of the second sample region may remain substantially constant in a situation where the bulk concentration $c_{M1}$ is varied. In this example, the drug cannot be bound to the human serum albumin of the functional layer of the second sample region, because the functional layer of the second sample region did not contain human serum albumin.

FIG. 7e also shows temporal evolution of the angular difference $\Delta\phi_{SPR,CH1}(t)$ of the first sample region, and temporal evolution of the angular difference $\Delta\phi_{TIR,CH1}(t)$ of the first sample region.

The term surface plasmon resonance (SPR) means collective oscillation of electrons in a solid or liquid, wherein said oscillation is stimulated by incident light B0. The resonance condition may be established when the frequency of photons substantially matches the natural frequency of oscillating surface electrons.

Surface plasmon polaritons are surface electromagnetic waves that propagate in a direction parallel to an interface between a metal layer 120 and a dielectric medium. A plasmon wave may propagate along the metal-dielectric interface 121. A change in the refractive index in the vicinity of the interface 121 and/or a change in the thickness of a molecular layer in the vicinity of the interface 121 may be monitored as a shift of the reflectivity curve.

The surface plasmon polaritons may be very sensitive to a change, which takes place in the vicinity of said interface 121. The change may be e.g. adsorption and/or desorption of molecules in the vicinity of said interface 121. The plasmons may exist when the real part of the complex permittivity of the metal layer 120 is negative, and the magnitude of the complex permittivity of the metal layer 120 is greater than the magnitude of the complex permittivity of the dielectric sample MX.

The surface plasmon polaritons may be excited e.g. by using Otto configuration or the Kretchmann configuration. In the Kretchmann configuration, the metal layer 120 may be deposited on the substrate 110, and the dielectric sample MX may be positioned on the metal layer 120. In the Otto configuration, the dielectric sample may be positioned in a narrow gap between a substrate and the metal film.

Surface plasmon resonance reflectivity measurements may be used e.g. for detecting molecular adsorption. The adsorbant molecules may be e.g. polymer molecules, DNA molecules, or protein molecules.

The measurement may be label-free, i.e. it is not necessary to attach label molecules to the adsorbant molecules. Adsorbed molecules may change the dielectric permittivity in the vicinity of the metal layer 120, which in turn may change the reflectivity. In particular, the change the dielectric permittivity may change the angular position of the minimum of the reflectivity curve. The angular position of the minimum of the reflectivity curve may be called as the surface plasmon resonance angle $\phi_{SPR}$.

The method may comprise measuring binding of an analyte M1 at the sample region REG1, wherein the sample region REG1 may comprise e.g. immobilized protein molecules, immobilized nucleotide molecules, immobilized nanoparticles, immobilized polymer molecules, immobilized lipid molecules, immobilized metal atoms, immobilized metal particles, immobilized inorganic compounds and/or immobilized carbohydrate molecules. In particular, the analyte M1 may be a drug, and the sample region REG1 may comprise immobilized organic molecules capable of binding to the molecules of the analyte M1. The immobilized organic molecules may be selected e.g. from a group consisting of protein molecules, nucleotide molecule and carbohydrate molecules.

The apparatus 500 may comprise a first sample region REG1. The apparatus 500 may comprise a first sample region REG1, and a second sample region REG2. The apparatus 500 may comprise one or more sample regions REG1, REG2. The apparatus 500 may comprise two or more sample regions REG1, REG2. The apparatus 500 may comprise three sample regions.

The method may comprise:
measuring a first surface plasmon resonance angle value ($\phi_{SPR,REF}$) of a sample region (REG1),
measuring a first critical angle value ($\phi_{TIR,REF}$) of the sample region (REG1),
causing a change of surface concentration ($c_{M1,SRF}$) of an analyte (M1) at the sample region (REG1),
changing the bulk composition at the sample region (REG1),
measuring a second surface plasmon resonance angle value ($\phi_{SPR}(t)$) of the sample region (REG1), measuring a second critical angle value ($\phi_{TIR}(t)$) of the sample region (REG1), and determining an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and wherein the magnitude ($\phi_{COMP}$) of said effect is determined from the second critical angle value ($\phi_{TIR}(t)$).

The measuring apparatus (500) may comprise at least one processor (CNT1), and a memory (MEM3) including computer program code (PROG1). The memory (MEM3) and the computer program code (PROG1) may be configured to, with the at least one processor (CNT1), cause the apparatus (500) to perform at least the following:

measure a first surface plasmon resonance angle value ($\phi_{SPR,REF}$) of a sample region (REG1) when the sample region (REG1) has a first surface concentration ($c_{M1,SRF}$) of an analyte (M1) and first bulk composition ($c_{M3}(t_{1A})$), measure a first critical angle value ($\phi_{TIR,REF}$) of the sample region (REG1), measure a second surface plasmon resonance angle value ($\phi_{SPR}(t)$) of the sample region (REG1) when the sample region (REG1) has a second surface concentration ($c_{M1,SRF}$) of an analyte (M1) and second bulk composition ($c_{M3}(t_{1B})$), measure a second critical angle value ($\phi_{TIR}(t)$) of the sample region (REG1), and determine an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and wherein the magnitude ($\phi_{COMP}$) of said effect is determined from the second critical angle value ($\phi_{TIR}(t)$).

The compensating angle function $f_1(\phi_{TIR})$ may have a slope $\Delta f_1(\phi_{TIR})/\Delta\phi_{TIR}$. The slope $\Delta f_1(\phi_{TIR})/\Delta\phi_{TIR}$ may be e.g. equal to a parameter C of a regression function (see e.g. equation 7c).

The magnitude $\phi_{COMP}$ of the effect of the bulk composition may be determined from the second critical angle value $\phi_{TIR}(t)$ by using a compensating angle function $f_1(\phi_{TIR})$, wherein the compensating angle function $f_1(\phi_{TIR})$ may be determined such that the slope (C) of the compensating angle function $f_1(\phi_{TIR})$ corresponds to the ratio of a change $\Delta\phi_{SPR12}$ of surface plasmon resonance angle to a change $\Delta\phi_{TIR12}$ of critical angle in a situation where the average refractive index $n_x$ at the sample region REG1 is changed.

The magnitude $\phi_{COMP}$ of the effect of the bulk composition may be determined from the second critical angle value $\phi_{TIR}(t)$ by using a compensating angle function $f_1(\phi_{TIR})$, wherein the compensating angle function $f_1(\phi_{TIR})$ may be determined such that the slope (C) of the compensating angle function $f_1(\phi_{TIR})$ corresponds to the ratio of a change $\Delta\phi_{SPR12}$ of surface plasmon resonance angle to a change $\Delta\phi_{TIR12}$ of critical angle in a situation where the concentration $c_{M3}$ of a substance M3 at the sample region REG1 is changed.

The method may comprise:

causing a first change $\Delta c_{M1,SRF}$ of surface concentration $c_{M1,SRF}$ of an analyte M1 at the sample region REG1, causing a second change $\Delta c_{M3}$ of bulk composition of a substance M3 at the sample region REG1, and determining an indicator value ($\phi_{AUX}(t)$) indicative of the change of the surface concentration ($c_{M1,SRF}$), wherein the indicator value ($\phi_{AUX}(t)$) is determined from the second surface plasmon resonance angle value ($\phi_{SPR}(t)$) by compensating an effect of the bulk composition, and determining the magnitude $\phi_{COMP}$ of said effect of the bulk composition from the second critical angle value $\phi_{TIR}(t)$ by using a compensating angle function $f_1(\phi_{TIR})$, wherein the compensating angle function $f_1(\phi_{TIR})$ may be determined such that the slope (C) of the compensating angle function $f_1(\phi_{TIR})$ corresponds to the ratio of a change $\Delta\phi_{SPR12}$ of surface plasmon resonance angle to a change $\Delta\phi_{TIR12}$ of critical angle in a calibration measurement where the concentration $c_{M3}$ of the substance M3 at the sample region REG1 is changed.

A first ratio R1 may be equal to the ratio of said first change to said second change, i.e.

$$R1 = \frac{\Delta c_{M1,SRF}}{\Delta c_{M3}} \tag{8a}$$

The calibration measurement may comprise keeping the surface concentration $c_{M1,SRF}$ of the analyte M1 constant, or by causing a third change $\Delta c_{M1,SRF,CAL}$ of the surface concentration $c_{M1,SRF}$ of the analyte M1. The calibration measurement may comprise causing a fourth change $\Delta c_{M3,CAL}$ of the concentration $c_{M3}$ of the substance M3. A second ratio R2 may be equal to the ratio of the third change to the fourth change, i.e.

$$R2 = \frac{\Delta c_{M1,SRF,CAL}}{\Delta c_{M3,CAL}} \tag{8b}$$

The concentration $c_{M1,SRF}$ of the analyte M1 and/or the concentration $c_{M3}$ of the substance M3 may be changed during said calibration measurement according to the second ratio R2, wherein the calibration measurement may be performed such that the second ratio R2 is substantially different from the first ratio R1, i.e. R2≠R1. For example, the concentration $c_{M3}$ of the substance M3 may be changed during said calibration measurement such that the change $\Delta c_{M1,SRF,CAL}$ of the surface concentration $c_{M1,SRF}$ of the analyte M1 during the calibration measurement is substantially smaller than said first change $\Delta c_{M1,SRF}$ of surface concentration $c_{M1,SRF}$ of said analyte M1. For example, the concentration $c_{M3}$ of the substance M3 may be changed during said calibration measurement such that the absolute value of R2 is e.g. smaller than 50% of the absolute value of R1:

$$|R2| < 0.5 \cdot |R1| \tag{8c}$$

For example, the concentration $c_{M3}$ of the substance M3 may be changed during said calibration measurement such that the absolute value of R2 is e.g. smaller than 30% of the absolute value of R1. For example, the concentration $c_{M3}$ of the substance M3 may be changed during said calibration measurement such that the absolute value of R2 is e.g. smaller than 10% of the absolute value of R1. For example, the calibration measurement may be performed such that the ratio R1 is different from zero but the absolute value of R2 is substantially equal to zero.

The magnitude $\phi_{COMP}$ of the effect of the bulk composition may be determined from the second critical angle value $\phi_{TIR}(t)$ by using a compensating angle function $f_1(\phi_{TIR})$, wherein the compensating angle function $f_1(\phi_{TIR})$ may be determined by fitting a regression function to data points such that the slope (C) of the compensating angle function $f_1(\phi_{TIR})$ corresponds to the ratio of a change $\Delta\phi_{SPR12}$ of surface plasmon resonance angle to a change $\Delta\phi_{TIR12}$ of critical angle in a situation where the average refractive index $n_x$ at the sample region REG1 is changed.

The magnitude of the effect of the bulk composition may be determined from the second critical angle value $\phi_{TIR}(t)$ by using a compensating angle function $f_1(\phi_{TIR})$, wherein the compensating angle function $f_1(\phi_{TIR})$ may be determined by fitting a regression function to data points, which have been calculated for a plurality of critical angle values according to the following equation:

$$\phi_{COMP}(t) = \arcsin\left[\frac{1}{n_G}\sqrt{\frac{\varepsilon_2 \cdot \varepsilon_x(t)}{\varepsilon_2 + \varepsilon_x(t)}}\right]$$

where $\phi_{COMP}$ denotes a compensating angle value, $n_G$ denotes the refractive index of the substrate 110, $\varepsilon_2$ denotes the real part of the dielectric permittivity of the conductive layer 120, and $\varepsilon_x(t)$ denotes a dielectric permittivity value calculated according to the following equation:

$$\varepsilon_x(t) = n_G^2 \sin^2 \phi_{TIR}(t)$$

where $\phi_{TIR}(t)$ denotes a critical angle value.

The magnitude of the effect of the bulk composition may be determined from the second critical angle value $\phi_{TIR}(t)$ according to the following equation:

$$\phi_{COMP}(t) = \arcsin\left[\frac{1}{n_G}\sqrt{\frac{\varepsilon_2 \cdot \varepsilon_x(t)}{\varepsilon_2 + \varepsilon_x(t)}}\right]$$

where $\phi_{COMP}$ denotes a compensating angle value, $n_G$ denotes the refractive index of the substrate 110, $\varepsilon_2$ denotes the real part of the dielectric permittivity of the conductive layer 120, and $\varepsilon_x(t)$ denotes a dielectric permittivity value calculated according to the following equation:

$$\varepsilon_x(t) = n_G^2 \sin^2 \phi_{TIR}(t)$$

where $\phi_{TIR}(t)$ denotes the second critical angle value.

The apparatus (500) may comprise:
a substrate (110) and a conductive layer (120) to form the sample region (REG1) together with a sample (MX), and
an optical detector (210) to monitor the intensity ($I_1$) of reflected light (B1) reflected by the sample region (REG1),
wherein the apparatus (500) is arranged to measure the reflectance ($I_1/I_0$, CRV2) of the sample region (REG1) as the function of the reflection angle ($\phi$) of the reflected light (B1), and to determine the second surface plasmon resonance angle value ($\phi_{SPR}(t)$) and the second critical angle value ($\phi_{TIR}(t)$) from the measured reflectance ($I_1/I_0$, CRV2).

The apparatus (500) may comprise:
a substrate (110) and a conductive layer (120) to form the sample region (REG1) together with a sample (MX),
an optical detector (210) to monitor the intensity ($I_1$) of reflected light (B1) reflected by the sample region (REG1), and
an actuator (320, 330) arranged to scan the reflection angle ($\phi$) of the reflected light (B1),
wherein the apparatus (500) is arranged to measure the reflectance ($I_1/I_0$, CRV2) of the sample region (REG1) as the function of the reflection angle ($\phi$), and to determine the second surface plasmon resonance angle value ($\phi_{SPR}(t)$) and the second critical angle value ($\phi_{TIR}(t)$) from the measured reflectance ($I_1/I_0$, CRV2).

The apparatus (500) may comprise:
a substrate (110) and a conductive layer (120) to form the sample region (REG1) together with a sample (MX),
an optical detector (210) to monitor the intensity ($I_1$) of reflected light (B1) reflected by the sample region (REG1), and
an actuator (320, 330) arranged to scan the reflection angle ($\phi$) of the reflected light (B1) by changing the direction of an input beam (B1) and/or by changing the position of the detector (210),
wherein the apparatus (500) is arranged to measure the reflectance ($I_1/I_0$, CRV2) of the sample region (REG1) as the function of the reflection angle ($\phi$), and to determine the second surface plasmon resonance angle value ($\phi_{SPR}(t)$) and the second critical angle value ($\phi_{TIR}(t)$) from the measured reflectance ($I_1/I_0$, CRV2).

The apparatus (500) may comprise:
a substrate (110) and a conductive layer (120) arranged to form the sample region (REG1) together with a sample (MX),
an optical detector (210) arranged to monitor the intensity ($I_1$) of reflected light (B1) reflected by the sample region (REG1), and
an actuator (320,330) arranged to scan the reflection angle ($\phi$) of the reflected light (B1) by changing the direction of an input beam (B0) and/or by changing the position of the detector 210,
wherein the apparatus (500) is arranged to measure a first reflectance curve (CRV1) when the sample region (REG1) has the first surface concentration ($c_{M1,SRF}$) and the first bulk composition ($c_{M3}(t_{1A})$), and the apparatus (500) is arranged to measure a second reflectance curve (CRV2) after changing the surface concentration and the bulk composition, wherein the first reflectance curve (CRV1) and the second reflectance curve (CRV2) specify reflectivity ($I_1/I_0$) of the sample region (REG1) as the function of the reflection angle ($\phi$).

In an embodiment, the reflection angle $\phi$ may also be scanned e.g. by moving a beam steering element positioned between the coupling element 220 and the detector 210. The beam steering element may be e.g. a mirror, a prism and/or a grating. The apparatus 500 may comprise one or more mirrors, one or more prisms and/or one or more gratings, which may be arranged to guide reflected light B1 from the coupling element 220 to the detector 210. The reflection angle $\phi$ may be scanned by moving a mirror, a prism and/or a grating positioned between the coupling element 220 and the detector 210. The apparatus 500 may comprise an actuator, which may be arranged to move a mirror, a prism and/or a grating positioned between the coupling element 220 and the detector 210.

The reflectance $I_1/I_0$ may also be measured as the function of the reflection angle $\phi$ without using an actuator to scan the reflection angle $\phi$. The apparatus 500 may comprise a light source, which may be arranged to simultaneously illuminate the sample region REG1 with a range of input angles $\phi'$, and the intensity $I_1$ of reflected light $I_1$ may be simultaneously monitored at a plurality of reflection angles $\phi$ by using a plurality of light detectors. The apparatus 500 may comprise a detector array, which comprises a plurality of light detectors. The detector array of the apparatus may be arranged to measure the intensity $I_1$ of reflected light $I_1$ as the function of the reflection angle $\phi$. The apparatus 500 may be arranged to determine the reflectance $I_1/I_0$ as the function of the reflection angle $\phi$ from the measured intensity $I_1$ of the reflected light $I_1$.

For the person skilled in the art, it will be clear that modifications and variations of the devices and the methods according to the present invention are perceivable. The figures are schematic. The particular embodiments described above with reference to the accompanying drawings are illustrative only and not meant to limit the scope of the invention, which is defined by the appended claims.

The invention claimed is:

1. A method, comprising:
    measuring a first surface plasmon resonance angle value of a sample region,
    measuring a first critical angle value of the sample region,
    causing a change of surface concentration of an analyte at the sample region,
    changing the bulk composition at the sample region,
    measuring a second surface plasmon resonance angle value of the sample region,
    measuring a second critical angle value of the sample region,
    determining an indicator value indicative of the change of the surface concentration, wherein the indicator value is determined from the second surface plasmon resonance angle value by compensating an effect of the bulk composition, and wherein the magnitude of said effect is determined by using the second critical angle value;
    wherein the sample region comprises a substrate and a conductive layer,
    wherein the method comprises using a coupling material to couple an input light beam from a coupling element into the substrate, and using the coupling material to couple a reflected beam from the substrate into the coupling element,
    wherein the magnitude of the effect of the bulk composition is determined from the second critical angle value according to the following equation:

$$\phi_{COMP}(t) = \arcsin\left[\frac{1}{n_G} \sqrt{\frac{\varepsilon_2 \cdot \varepsilon_x(t)}{\varepsilon_2 + \varepsilon_x(t)}}\right]$$

where $\phi_{COMP}$ denotes a compensating angle value, $n_G$ denotes the refractive index of the substrate, $\varepsilon_2$ denotes the real part of the dielectric permittivity of the conductive layer, and $\varepsilon_x(t)$ denotes a dielectric permittivity value calculated according to the following equation:

$$\varepsilon_x(t) = n_G^2 \sin^2 \phi_{TIR}(t)$$

where $\phi_{TIR}(t)$ denotes the second critical angle value.

2. The method of claim 1, wherein the analyte is a drug, and the sample region comprises immobilized organic molecules capable of binding to the molecules of the analyte.

3. The method of claim 2 wherein the immobilized organic molecules have been selected from a group consisting of protein molecules, nucleotide molecule and carbohydrate molecules.

4. The method of claim 1, wherein the sample region comprises immobilized protein molecules, immobilized nucleotide molecules, immobilized nanoparticles, immobilized polymer molecules, immobilized lipid molecules, immobilized metal atoms, immobilized metal particles, immobilized inorganic compounds and/or immobilized carbohydrate molecules.

5. The method of claim 1 comprising varying the bulk concentration of a stabilizing additive.

6. The method of claim 1 comprising varying the bulk concentration of a solubility-enhancing additive.

* * * * *